US007157569B2

(12) United States Patent
Wallace et al.

(10) Patent No.: US 7,157,569 B2
(45) Date of Patent: Jan. 2, 2007

(54) MUTATION ASSOCIATED WITH EPILEPSY

(75) Inventors: Robyn Heather Wallace, St. Marys (AU); John Charles Mulley, Firle (AU); Samuel Frank Berkovic, Caulfield (AU); Louise Anne Harkin, Salisbury-East (AU); Leanne Michelle Dibbens, College Park (AU)

(73) Assignee: Bionomics Limited, Thebarton (AU)

( * ) Notice: Subject to any disclaimer, the term of this patent is extended or adjusted under 35 U.S.C. 154(b) by 292 days.

(21) Appl. No.: 10/312,184

(22) PCT Filed: Jun. 20, 2001

(86) PCT No.: PCT/AU01/00729

§ 371 (c)(1),
(2), (4) Date: Apr. 9, 2003

(87) PCT Pub. No.: WO01/98486

PCT Pub. Date: Dec. 27, 2001

(65) Prior Publication Data

US 2004/0038236 A1    Feb. 26, 2004

(30) Foreign Application Priority Data

Jun. 20, 2000  (AU)  ................... PQ 8260
Sep. 13, 2000  (AU)  ................... PR 0098
May 11, 2001  (AU)  ................... PR 4953

(51) Int. Cl.
*C07K 14/705* (2006.01)
*C12N 15/12* (2006.01)
(52) U.S. Cl. .................... 536/23.5; 435/6; 435/69.1; 435/252.3; 435/320.1
(58) Field of Classification Search .................... None
See application file for complete search history.

(56) References Cited

U.S. PATENT DOCUMENTS 5,654,172 A    8/1997  Li et al.  ................... 435/69.1

OTHER PUBLICATIONS

Mohler, Genetic Approaches to CNS Disorderes with Particular Reference to GAGAA-Receptor Mutations, J. of Receptor & Signal Transduction Research 17(1-3):1-10, 1997.*
Pritchett et al. *Importance of a novel GABA$_A$ receptor subunit for benzodiazepine pharmacology*, Nature 338:582-585 (Apr. 13, 1989).
Horlick et al., *Cominatorial gene expression using multiple episomal vectors*, Gene 243:187-194 (2000).
Shivers et al., *Two Novel GABA$_A$ Receptor Subunits Exist in Distinct Neuronal Subpopulations*, Neuron 3:327-337 (Sep. 1989).
Jiang et al., *Complete Genomic Sequence of 195 Kb of Human DNA Containing the Gene GABRG2*, DNA Sequence 11:373-382 (2000).

Baulac et al., *First genetic evidence of GABA$_A$ receptor dysfunction in epilepsy: a mutation in the γ2-subunit gene*, Nature Genetics 28:46-48 (May 2001).
Wallace et al., *Mutant GABA$_A$ receptor γ2-subunit in childhood absence epilepsy and febrile seizures*, Nature Genetics 28:49-52 (May 2001).
Oruč et al., *Positive Association between the GABRA5 Gene and Unipolar Recurrent Major Depression*, Neuropsychobiology 36:62-64 (1997),
Annegers, Chapter 11: *The Epidemiology of Epilepsy*, The Treatment of Epilepsy: Principles and Practice 2$^{nd}$ Ed. pp. 165-172 (1996).
Berkovic et al., *Concepts of absence epilepsies: Discrete syndromes or biological continuum?*, Neurology 37, No. 6:993-1000 (Jun. 1987).
Berkovic et al., Chapter 5: *The epilepsies: specific syndromes or a neurobiological continuum?*, Epileptic Seizures and Syndromes pp. 25-37 (1994).
Biervert et al., *A Potassium Channel Mutation in Neonatal Human Epilepsy*, Science 279:403-406 (Jan. 16, 1998).
Blasi, *Influence of Benzodiazepines on Body Weight and Food Intake in Obese and Lean Zucker Rats*, Prog. Neuro-Psychoparmacol. & Biol. Psychiat. 24:561-577 (2000).
Brooks-Kayal et al., *Developmental Changes in Human γ-Aminobutric Acid$_A$ Receptor Subunit Composition*, Annals of Neurology 34, No. 5:687-693 (Nov. 1993).
Charlier et al., *A pore mutation in a novel KQT-like potassium channel gene in an idiopathic epilepsy family*, Nature Genetics 18:53-55 (Jan. 1998).
Commision on Classification and Teminology of the International League Against Epilepsy, *Proposal for Revised Classification of Epilepsies and Epileptic Syndromes*, Epilepsia 30(4):389-399 (1989).
Destexhe, *Can GABA$_A$ conductances explain the fast oscillation frequency of absence seizures in rodents?*, European J. of Neuroscience 11:2175-2181 (1999).
Draguhn et al., *Functional and Molecular Distinction between Recombinant Rat GABA$_A$ Receptor Subtypes by Zn$^{2+}$*, Neuron 5:781-788 (1990).
Feucht et al., *Possible Association between Childhood Absence Epilepsy and the Gene Encoding GABRB3*, Biol. Psychiatry 46:997-1002 (1999).

(Continued)

*Primary Examiner*—John Ulm
(74) *Attorney, Agent, or Firm*—Jenkins, Wilson, Taylor, & Hunt, P.A.

(57) ABSTRACT

An isolated mammalian DNA molecule encoding a mutant γ-aminobutyric acid (GABA) receptor subunit, wherein a mutation event selected from the group consisting of point mutations, deletions, insertions and rearrangements has occurred and said mutation event disrupts the functioning of an assembled GABA receptor, or an otherwise functional fragment or homologue thereof.

17 Claims, 6 Drawing Sheets

OTHER PUBLICATIONS

Futatsugi et al., *Mechanisms of generalized absence epilepsy*, Brain & Development 20:75-79 (1998).

Gardiner, *Impact of our understanding of the genetic aetiology of epilepsy*, J. Neurol 247:327-334 (2000).

Gerner et al., *CSF GABA in Normal Subjects and Patients with Depression, Schizophrenia, Mania, and Anorexia Nervosa*, Am J. Psychiatry 138, 8:1098-1101 (Aug. 1981).

Jackson, *Ligant-gated Channel: Postsynaptic Receptors and Drug Targets, Chapter 32: Jasper's Basic Mechanisms of the Epilepsies (3rd ed.)*: Advances in Neurology 79:511-524 (1999).

Kucken et al., *Identification of Benzodiazepine Binding Site Residues in the γ2 Subunit of the γ-Aminobutyric Acid$_A$ Receptor*, MOL 57:932-939 (2000).

Limmroth et al., *GABA$_A$-receptor-mediated effects of progesterone, its ring-A-reduce metabolites and synthetic neuroactive steroids on neurogenic oedema in the rat meninges*, British J. of Pharmacology 117:99-104 (1996).

Mitsikostas et al., *Receptor systems mediating c-fos expression within trigeminal nucleus caudalis in animal models of migraine*, Brain Research Reviews 35:20-35 (2001).

Olsen et al., *GABA Receptor Function and Epilepsy, Chapter 31, Jasper's Basic Mechanisms of the Epilepsies (3rd Ed.): Advances in Neurology* 79:499-510 (1999).

Papadimitriou et al., *Association Between the GABA$_A$ Receptor $\alpha_5$ Subunit Gene Locus (GABRA$_5$) AND Bipolar Affective Disorder*, American J. of Medical Genetics (Neuropsychiatric Genetics) 81:73-80 (1998).

Pearlson et al., *Neurobiology of Schizophrenia*, Annals of Neurology 48(4):556-566 (Oct. 2000).

Reutens et al., *Idiopathic generalized epilepsy of adolescence: Are the syndromes clinically distinct?*, Neurology 45:1469-1476 (Aug. 1995).

Scheffer et al., *Generalized epilepsy with febrile seizures plus a genetic disorder with heterogeneous clinical phenotypes*, Brain 120:479-490 (1997).

Sibille et al., *Genetic Inactivation of the Serotonin$_{1A}$ Receptor in Mice Results in Downregulation of Major GABA$_A$ Receptor $\alpha$ Subunits, Reduction of GABA$_A$ Receptor Binding, and Benzodiazepine-Resistant Anxiety*, The J. of Neuroscience 20(8):2458-2765 (Apr. 15, 2000).

Sigel et al., *The benzodiazepine binding site of GABA$_A$ receptors*, TiPS 18:425-429 (Nov. 1997).

Singh et al., *A novel potassium channel gene, KCNQ2, is mutated in an inherited epilepsy of newborns*, Nature Genetics 18:25-29 (Jan. 1998).

Singh et al., *Generalized Epilepsy with Febrile Seizures Plus: A Common Childhood-Onset Genetic Epilepsy Syndrome*, Annals of Neurology 45(1):75-91 (Jan. 1999).

Vergnes et al., *Selective Susceptibility in Ihibitors of GABA Synthesis and Antagonists of GABA$_A$ Receptor in Rats with Genetic Absence Epilepsy*, Experimental Neurology 161:714-723 (2000).

Wallace et al., *Febrile seizures and generalized epilepsy associated with a mutation in the Na$^\circ$-channel β1 subunit gene SCN1B*, Nature Genetics 19:366-370 (Aug. 1998).

Wallace et al., *Mutant GABA$_A$ receptor γ2-subunit in childhood absence epilepsy and febrile seizures*, Nature Genetics 28:49-52 (May 2001).

Mizukami et al., *GABA$_A$ receptor β2 and β3 subunits mRNA in the hippocampal formation of aged human brain with Alzheimer-related neuropathology*, Molecular Brain Research 56:268-272 (1998).

Mizukami et al., *Immunohistochemical study of GABA$_A$ receptor α1 subunit in the hippocampal formation of aged brains with Alzheimer-related neurophathlogic changes*, Brain Research 299:148-155 (1998).

Buhr and Sigel, *A point mutation in the γ$_2$ subunit of γ-aminobutyric acid type A receptors results in altered benzodiazepine binding site specificity*, Proc. Natl. Acad. Sci. USA 94:8824-8829 (Aug. 1997).

Carlson et al., *A Single Gylcine Residue at the Entrance to the First Membrane-Spanning Domain of the γ-Aminobutyric Acid Type A Receptor β$_2$ Subunit Affects Allosteric Sensitivity to GABA and Anesthetics*, Molecular Pharmacology 57:474-484 (2000).

Chang and Weiss, *Allosteric Activation Mechanism of the α1β2 γ2 γ-Aminobutyric Acid Type A Receptor Revealed by Mutation of the Conserved M2 Leucine*, Biophysical Journal 77:2542-2551 (Nov. 1999).

Supplementary European Search Report for PCB/P04121PEP dated Oct. 12, 2004.

Database UNIPROT Nov. 1, 1990 "Protein GAC2$_{13}$ Human" XP002296405 retrieved from EBI databases accession No. P18507 Q9UN15.

Database UNIPROT Jul. 15, 1998 "GAD$_{13}$ Human" XP002296406 retrieved from EBI database accession No. 014764.

Korpi et al. Benzodiazepine-induced motor impairment linked to point mutation in cerebellar GABA-A receptor Nature 361:356-359 (1993).

Delorey et al., "Mice Lacking the β 3 Subunit of the GABA A Receptor Have the Epilepsy Phenotype and Many of the Behavioral Characteristics of Angelman Syndrome", *The Journal of Neuroscience*, 18(20):8505-8514, Oct. 1998.

* cited by examiner

Figure 3

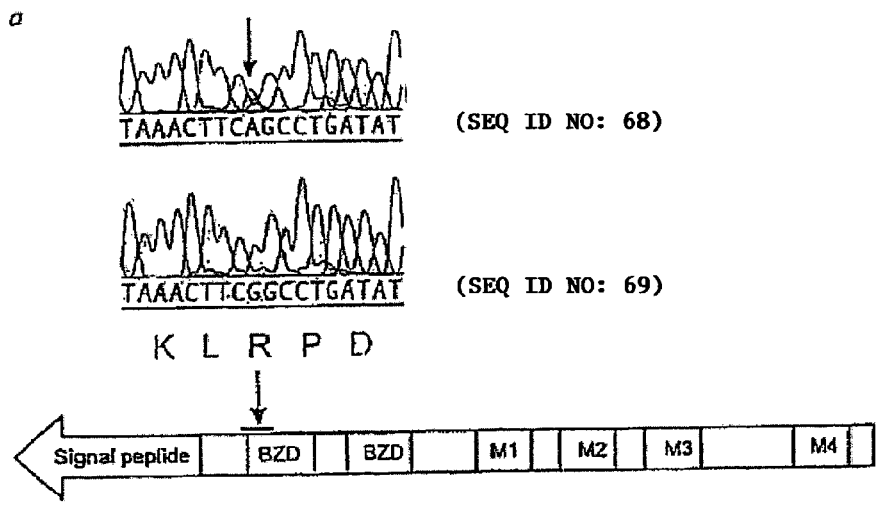

| Protein | Accession | Amino Acid Sequence | |
|---|---|---|---|
| GABRG2 (R43Q) | - | G Y D N K L Q P D I G V | (SEQ ID NO:70) |
| GABRG2 | NP_000807 | G Y D N K L R P D I G V | (SEQ ID NO:71) |
| GABRB1 | NP_000803 | G Y D I R L R P D E G G | (SEQ ID NO:72) |
| GABRA1 | NP_000797 | G Y D N R L R P G L G E | (SEQ ID NO:73) |
| GLRA1 | NP_000162 | G Y D A R I R P N E K G | (SEQ ID NO:74) |
| GLRB1 | NP_000815 | S Y D P R I R P N F K G | (SEQ ID NO:75) |
| CHRNA4 | NP_000735 | G Y N K W S R P V G N I | (SEQ ID NO:76) |
| CHRNB4 | NP_000739 | R Y N K L I R P A V N S | (SEQ ID NO:77) |
| HTR3A | NP_000860 | N Y R K G V R P V R D W | (SEQ ID NO:78) |
| MOUSE-Gabrgq2 | NP_032099 | G Y D N K L R P D I G V | (SEQ ID NO:79) |
| DROS-LCCH3 | AAE48540 | G Y D I R L R P N F G G | (SEQ ID NO:80) |
| C. ELEG-gbr-2 | AAC25481 | D Y D W R V R P R G M N | (SEQ ID NO:81) |

SEQUENCE LISTING

<160> NUMBER OF SEQ ID NOS: 51

<210> SEQ ID NO 1
<211> LENGTH: 1745
<212> TYPE: DNA
<213> ORGANISM: Homo sapiens

<400> SEQUENCE: 1

```
cctgacgctt tgatggtatc tgcaagcgtt tttgctgatc ttatctctgc cccctgaata      60
ttaattccct aatctggtag caatccatct ccccagtgaa ggacctacta gaggcaggtg     120
gggggagcca ccatcagatc atcaagcata agaataatac aaaggggagg gattcttctg     180
caaccaagag gcaagaggcg agagaaggaa aaaaaaaaaa aaagcgatga gttcaccaaa     240
tatatggagc acaggaagct cagtctactc gactcctgta ttttcacaga aaatgacggt     300
gtggattctg ctcctgctgt cgctctaccc tggcttcact agccagaaat ctgatgatga     360
ctatgaagat tatgcttcta acaaaacatg ggtcttgact ccaaaagttc ctgagggtga     420
tgtcactgtc atcttaaaca acctgctgga aggatatgac aataaacttc agcctgtatt     480
aggagtgaag ccaacgttaa ttcacacaga catgtatgtg aatagcattg gtccagtgaa     540
cgctatcaat atggaataca ctattgatat attttttgcg caaatgtggt atgacagacg     600
tttgaaattt aacagcacca ttaaagtcct ccgattgaac agcaacatgg tggggaaaat     660
ctggattcca gacactttct tcagaaattc caaaaaagct gatgcacact ggatcaccac     720
ccccaacagg atgctgagaa tttggaatga tggtcgagtg ctctactccc taaggttgac     780
```

-continued

```
aattgatgct gagtgccaat tacaattgca caattttcca atggatgaac actcctgccc    840
cttggagttc tccagttatg gctatccacg tgaagaaatt gtttatcaat ggaagcgaag    900
ttctgttgaa gtgggcgaca caagatcctg gaggctttat caattctcat tgttggtct     960 aagaaatacc accgaagtag tgaagacaac ttccggagat tatgtggtca tgtctgtcta   1020
ctttgatctg agcagaagaa tgggatactt taccatccag acctatatcc cctgcacact   1080
cattgtcgtc ctatcctggg tgtcttctg gatcaataag gatgctgttc cagccagaac    1140
atctttaggt atcaccactg tcctgacaat gaccaccctc agcaccattg cccggaaatc   1200
gctccccaag gtctcctatg tcacagcgat ggatctcttt gtatctgttt gtttcatctt   1260
tgtcttctct gctctggtgg agtatggcac cttgcattat tttgtcagca accggaaacc   1320
aagcaaggac aaagataaaa agaagaaaaa ccctgcccct accattgata tccgcccaag   1380
atcagcaacc attcaaatga ataatgctac acaccttcaa gagagagatg aagagtacgg   1440
ctatgagtgt ctggacggca aggactgtgc cagttttttc tgctgttttg aagattgtcg   1500
aacaggagct tggagacatg ggaggataca tatccgcatt gccaaaatgg actcctatgc   1560
tcggatcttc ttccccactg ccttctgcct gtttaatctg gtctattggg tctcctacct   1620
ctacctgtga ggaggtatgg gttttactga tatggttctt attcactgag tctcatggag   1680
agatgtctgt tctaagtcca cttaaataat cctctatgtg gttgataagt atctgaatct   1740
gtttc                                                               1745

<210> SEQ ID NO 2
<211> LENGTH: 1745
<212> TYPE: DNA
<213> ORGANISM: Homo sapiens

<400> SEQUENCE: 2
cctgacgctt tgatggtatc tgcaagcgtt tttgctgatc ttatctctgc ccctgaata     60 ttaattccct aatctggtag caatccatct ccccagtgaa ggacctacta gaggcaggtg    120
gggggagcca ccatcagatc atcaagcata agaataatac aaaggggagg gattcttctg    180
caaccaagag gcaagaggcg agagaaggaa aaaaaaaaaa aaagcgatga gttcaccaaa    240
tatatggagc acaggaagct cagtctactc gactcctgta ttttcacaga aaatgacggt    300
gtggattctg ctcctgctgt cgctctaccc tggcttcact agccagaaat ctgatgatga    360
ctatgaagat tatgcttcta acaaaacatg ggtcttgact ccaaaagttc ctgagggtga    420
tgtcactgtc atcttaaaca acctgctgga aggatatgac aataaacttc ggcctgatat    480
aggagtgaag ccaacgttaa ttcacacaga catgtatgtg aatagcattg gtccagtgaa    540
cgctatcaat atgaaataca ctattgatat atttttttgcg caaatgtggt atgacagacg    600
tttgaaattt aacagcacca ttaaagtcct ccgattgaac agcaacatgg tggggaaaat    660
ctggattcca gacactttct tcagaaattc caaaaaagct gatgcacact ggatcaccac    720
ccccaacagg atgctgagaa tttggaatga tggtcgagtg ctctactccc taaggttgac    780
aattgatgct gagtgccaat tacaattgca caattttcca atggatgaac actcctgccc    840
cttggagttc tccagttatg gctatccacg tgaagaaatt gtttatcaat ggaagcgaag    900
ttctgttgaa gtgggcgaca caagatcctg gaggctttat caattctcat tgttggtct     960 aagaaatacc accgaagtag tgaagacaac ttccggagat tatgtggtca tgtctgtcta   1020
ctttgatctg agcagaagaa tgggatactt taccatccag acctatatcc cctgcacact   1080
cattgtcgtc ctatcctggg tgtcttctg gatcaataag gatgctgttc cagccagaac    1140
```

-continued

```
atctttaggt atcaccactg tcctgacaat gaccaccctc agcaccattg cccggaaatc    1200
gctccccaag gtctcctatg tcacagcgat ggatctcttt gtatctgttt gtttcatctt    1260
tgtcttctct gctctggtgg agtatggcac cttgcattat tttgtcagca accggaaacc    1320
aagcaaggac aaagataaaa agaagaaaaa ccctgcccct accattgata tccgcccaag    1380
atcagcaacc atttaaatga ataatgctac acaccttcaa gagagagatg aagagtacgg    1440
ctatgagtgt ctggacggca aggactgtgc cagttttttc tgctgttttg aagattgtcg    1500
aacaggagct tggagacatg ggaggataca tatccgcatt gccaaaatgg actcctatgc    1560
tcggatcttc ttccccactg ccttctgcct gtttaatctg gtctattggg tctcctacct    1620
ctacctgtga ggaggtatgg gttttactga tatggttctt attcactgag tctcatggag    1680
agatgtctgt tctaagtcca cttaaataat cctctatgtg gttgataagt atctgaatct    1740
gtttc                                                                 1745
```

<210> SEQ ID NO 3
<211> LENGTH: 1359
<212> TYPE: DNA
<213> ORGANISM: Homo sapiens

<400> SEQUENCE: 3

```
atggacgcgc ccgcccggct gctggcccg ctcctgctcc tctgcgcgca gcagctccgc       60
ggcaccagag cgatgaatga catcggcgac tacgtgggct ccaacctgga gatctcctgg    120
ctccccaacc tggacgggct gatagccggc tacgcccgca acttccggcc tggcatcgga    180 ggccccccg tgaatgtggc ccttgccctg gaggtggcca gcatcgacca catctcagag    240
gccaacatgg agtacaccat gacggtgttc ctgcaccaga gctggcggga cagcaggctc    300
tcctacaacc acaccaacga gaccctgggc ctggacagcc gcttcgtgga caagctgtgg    360
ctgcccgaca ccttcatcgt gaacgccaag tcggcctggt ccacgacgt gacggtggag    420 aacaagctca tccggctgca gcccgacggc gtgatcctgt acagcatccg aatcacctcc    480
actgtggcct gcgacatgga cctggccaaa taccccatgg acgagcagga gtgcatgctg    540
gacctggaga gctacggtta tcatcggag gacatcgtct actactggtc ggagagccag    600
gagcacatcc acgggctgga caagctgcag ctggcgcagt tcaccatcac cagctactgc    660
ttcaccacgg agctgatgaa cttcaagtcc gctggccagt tccacggct cagcctgcac    720 ttccacctgc ggaggaaccg cggcgtgtac atcatccaat cctacatgcc ctccgtcctg    780
ctggtcgcca tgtcctgggt ctccttctgg atcagccagg cggcggtgcc cgccagggtg    840
tctctaggca tcaccacggt gctgacgatg accacgctca tggtcagtgc ccgctcctcc    900
ctgccacggg catcagccat caaggcactg gacgtctact ctggatctg ctatgtcttc    960 gtgtttgccg ccctggtgga gtacgccttt gctcatttca acgccgacta caggaagaag    1020
cagaaggcca aggtcaaggt ctccaggccg agggcagaga tggacgtgag gaacgccatt    1080
gtcctcttct ccctctctgc tgccggcgt acgcaggagc tggccatctc cgccggcag    1140 cgccgcgtcc cggggaacct gatgggctcc tacaggtcgg tgggggtgga gacaggggag    1200
acgaagaagg aggggcagc ccgctcagga ggccagggg gcatccgtgc ccggctcagg    1260
cccatcgacg cagacaccat tgacatttac gcccgcgctg tgttccctgc ggcgtttgcg    1320
gccgtcaatg tcatctactg gcggcatac gccatgtga                              1359
```

<210> SEQ ID NO 4

```
<211> LENGTH: 467
<212> TYPE: PRT
<213> ORGANISM: Homo sapiens

<400> SEQUENCE: 4

Met Ser Ser Pro Asn Ile Trp Ser Thr Gly Ser Ser Val Tyr Ser Thr
1               5                   10                  15

Pro Val Phe Ser Gln Lys Met Thr Val Trp Ile Leu Leu Leu Leu Ser
            20                  25                  30

Leu Tyr Pro Gly Phe Thr Ser Gln Lys Ser Asp Asp Tyr Glu Asp
        35                  40                  45

Tyr Ala Ser Asn Lys Thr Trp Val Leu Thr Pro Lys Val Pro Glu Gly
    50                  55                  60

Asp Val Thr Val Ile Leu Asn Asn Leu Leu Glu Gly Tyr Asp Asn Lys
65                  70                  75                  80

Leu Gln Pro Asp Ile Gly Val Lys Pro Thr Leu Ile His Thr Asp Met
                85                  90                  95

Tyr Val Asn Ser Ile Gly Pro Val Asn Ala Ile Asn Met Glu Tyr Thr
            100                 105                 110

Ile Asp Ile Phe Phe Ala Gln Met Trp Tyr Asp Arg Arg Leu Lys Phe
        115                 120                 125

Asn Ser Thr Ile Lys Val Leu Arg Leu Asn Ser Asn Met Val Gly Lys
130                 135                 140

Ile Trp Ile Pro Asp Thr Phe Phe Arg Asn Ser Lys Lys Ala Asp Ala
145                 150                 155                 160

His Trp Ile Thr Thr Pro Asn Arg Met Leu Arg Ile Trp Asn Asp Gly
                165                 170                 175

Arg Val Leu Tyr Ser Leu Arg Leu Thr Ile Asp Ala Glu Cys Gln Leu
            180                 185                 190

Gln Leu His Asn Phe Pro Met Asp Glu His Ser Cys Pro Leu Glu Phe
        195                 200                 205

Ser Ser Tyr Gly Tyr Pro Arg Glu Glu Ile Val Tyr Gln Trp Lys Arg
210                 215                 220

Ser Ser Val Glu Val Gly Asp Thr Arg Ser Trp Arg Leu Tyr Gln Phe
225                 230                 235                 240

Ser Phe Val Gly Leu Arg Asn Thr Thr Glu Val Val Lys Thr Thr Ser
                245                 250                 255

Gly Asp Tyr Val Val Met Ser Val Tyr Phe Asp Leu Ser Arg Arg Met
            260                 265                 270

Gly Tyr Phe Thr Ile Gln Thr Tyr Ile Pro Cys Thr Leu Ile Val Val
        275                 280                 285

Leu Ser Trp Val Ser Phe Trp Ile Asn Lys Asp Ala Val Pro Ala Arg
290                 295                 300

Thr Ser Leu Gly Ile Thr Thr Val Leu Thr Met Thr Thr Leu Ser Thr
305                 310                 315                 320

Ile Ala Arg Lys Ser Leu Pro Lys Val Ser Tyr Val Thr Ala Met Asp
                325                 330                 335

Leu Phe Val Ser Val Cys Phe Ile Phe Val Phe Ser Ala Leu Val Glu
            340                 345                 350

Tyr Gly Thr Leu His Tyr Phe Val Ser Asn Arg Lys Pro Ser Lys Asp
        355                 360                 365

Lys Asp Lys Lys Lys Lys Asn Pro Ala Pro Thr Ile Asp Ile Arg Pro
370                 375                 380

Arg Ser Ala Thr Ile Gln Met Asn Asn Ala Thr His Leu Gln Glu Arg
```

```
                385                 390                 395                 400
Asp Glu Glu Tyr Gly Tyr Glu Cys Leu Asp Gly Lys Asp Cys Ala Ser
                405                 410                 415

Phe Phe Cys Cys Phe Glu Asp Cys Arg Thr Gly Ala Trp Arg His Gly
            420                 425                 430

Arg Ile His Ile Arg Ile Ala Lys Met Asp Ser Tyr Ala Arg Ile Phe
        435                 440                 445

Phe Pro Thr Ala Phe Cys Leu Phe Asn Leu Val Tyr Trp Val Ser Tyr
    450                 455                 460

Leu Tyr Leu
465

<210> SEQ ID NO 5
<211> LENGTH: 389
<212> TYPE: PRT
<213> ORGANISM: Homo sapiens

<400> SEQUENCE: 5

Met Ser Ser Pro Asn Ile Trp Ser Thr Gly Ser Ser Val Tyr Ser Thr
1               5                   10                  15

Pro Val Phe Ser Gln Lys Met Thr Val Trp Ile Leu Leu Leu Leu Ser
            20                  25                  30

Leu Tyr Pro Gly Phe Thr Ser Gln Lys Ser Asp Asp Asp Tyr Glu Asp
        35                  40                  45

Tyr Ala Ser Asn Lys Thr Trp Val Leu Thr Pro Lys Val Pro Glu Gly
50                  55                  60

Asp Val Thr Val Ile Leu Asn Asn Leu Leu Glu Gly Tyr Asp Asn Lys
65                  70                  75                  80

Leu Arg Pro Asp Ile Gly Val Lys Pro Thr Leu Ile His Thr Asp Met
                85                  90                  95

Tyr Val Asn Ser Ile Gly Pro Val Asn Ala Ile Asn Met Glu Tyr Thr
            100                 105                 110

Ile Asp Ile Phe Phe Ala Gln Met Trp Tyr Asp Arg Arg Leu Lys Phe
        115                 120                 125

Asn Ser Thr Ile Lys Val Leu Arg Leu Asn Ser Asn Met Val Gly Lys
    130                 135                 140

Ile Trp Ile Pro Asp Thr Phe Phe Arg Asn Ser Lys Lys Ala Asp Ala
145                 150                 155                 160

His Trp Ile Thr Thr Pro Asn Arg Met Leu Arg Ile Trp Asn Asp Gly
                165                 170                 175

Arg Val Leu Tyr Ser Leu Arg Leu Thr Ile Asp Ala Glu Cys Gln Leu
            180                 185                 190

Gln Leu His Asn Phe Pro Met Asp Glu His Ser Cys Pro Leu Glu Phe
        195                 200                 205

Ser Ser Tyr Gly Tyr Pro Arg Glu Glu Ile Val Tyr Gln Trp Lys Arg
    210                 215                 220

Ser Ser Val Glu Val Gly Asp Thr Arg Ser Trp Arg Leu Tyr Gln Phe
225                 230                 235                 240

Ser Phe Val Gly Leu Arg Asn Thr Thr Glu Val Val Lys Thr Thr Ser
                245                 250                 255

Gly Asp Tyr Val Val Met Ser Val Tyr Phe Asp Leu Ser Arg Arg Met
            260                 265                 270

Gly Tyr Phe Thr Ile Gln Thr Tyr Ile Pro Cys Thr Leu Ile Val Val
        275                 280                 285
```

-continued

```
Leu Ser Trp Val Ser Phe Trp Ile Asn Lys Asp Ala Val Pro Ala Arg
    290                 295                 300

Thr Ser Leu Gly Ile Thr Thr Val Leu Thr Met Thr Thr Leu Ser Thr
305                 310                 315                 320

Ile Ala Arg Lys Ser Leu Pro Lys Val Ser Tyr Val Thr Ala Met Asp
                325                 330                 335

Leu Phe Val Ser Val Cys Phe Ile Phe Val Phe Ser Ala Leu Val Glu
                340                 345                 350

Tyr Gly Thr Leu His Tyr Phe Val Ser Asn Arg Lys Pro Ser Lys Asp
            355                 360                 365

Lys Asp Lys Lys Lys Lys Asn Pro Ala Pro Thr Ile Asp Ile Arg Pro
370                 375                 380

Arg Ser Ala Thr Ile
385
```

<210> SEQ ID NO 6
<211> LENGTH: 452
<212> TYPE: PRT
<213> ORGANISM: Homo sapiens

<400> SEQUENCE: 6

```
Met Asp Ala Pro Ala Arg Leu Leu Ala Pro Leu Leu Leu Leu Cys Ala
1               5                   10                  15

Gln Gln Leu Arg Gly Thr Arg Ala Met Asn Asp Ile Gly Asp Tyr Val
                20                  25                  30

Gly Ser Asn Leu Glu Ile Ser Trp Leu Pro Asn Leu Asp Gly Leu Ile
            35                  40                  45

Ala Gly Tyr Ala Arg Asn Phe Arg Pro Gly Ile Gly Gly Pro Pro Val
        50                  55                  60

Asn Val Ala Leu Ala Leu Glu Val Ala Ser Ile Asp His Ile Ser Glu
65                  70                  75                  80

Ala Asn Met Glu Tyr Thr Met Thr Val Phe Leu His Gln Ser Trp Arg
                85                  90                  95

Asp Ser Arg Leu Ser Tyr Asn His Thr Asn Glu Thr Leu Gly Leu Asp
                100                 105                 110

Ser Arg Phe Val Asp Lys Leu Trp Leu Pro Asp Thr Phe Ile Val Asn
            115                 120                 125

Ala Lys Ser Ala Trp Phe His Asp Val Thr Val Glu Asn Lys Leu Ile
        130                 135                 140

Arg Leu Gln Pro Asp Gly Val Ile Leu Tyr Ser Ile Arg Ile Thr Ser
145                 150                 155                 160

Thr Val Ala Cys Asp Met Asp Leu Ala Lys Tyr Pro Met Asp Glu Gln
                165                 170                 175

Glu Cys Met Leu Asp Leu Glu Ser Tyr Gly Tyr Ser Ser Glu Asp Ile
                180                 185                 190

Val Tyr Tyr Trp Ser Glu Ser Gln Glu His Ile His Gly Leu Asp Lys
            195                 200                 205

Leu Gln Leu Ala Gln Phe Thr Ile Thr Ser Tyr Cys Phe Thr Thr Glu
    210                 215                 220

Leu Met Asn Phe Lys Ser Ala Gly Gln Phe Pro Arg Leu Ser Leu His
225                 230                 235                 240

Phe His Leu Arg Arg Asn Arg Gly Val Tyr Ile Ile Gln Ser Tyr Met
                245                 250                 255

Pro Ser Val Leu Leu Val Ala Met Ser Trp Val Ser Phe Trp Ile Ser
                260                 265                 270
```

-continued

```
Gln Ala Ala Val Pro Ala Arg Val Ser Leu Gly Ile Thr Thr Val Leu
        275                 280                 285

Thr Met Thr Thr Leu Met Val Ser Ala Arg Ser Ser Leu Pro Arg Ala
    290                 295                 300

Ser Ala Ile Lys Ala Leu Asp Val Tyr Phe Trp Ile Cys Tyr Val Phe
305                 310                 315                 320

Val Phe Ala Ala Leu Val Glu Tyr Ala Phe Ala His Phe Asn Ala Asp
                325                 330                 335

Tyr Arg Lys Lys Gln Lys Ala Lys Val Lys Val Ser Arg Pro Arg Ala
            340                 345                 350

Glu Met Asp Val Arg Asn Ala Ile Val Leu Phe Ser Leu Ser Ala Ala
        355                 360                 365

Gly Val Thr Gln Glu Leu Ala Ile Ser Arg Arg Gln Arg Arg Val Pro
    370                 375                 380

Gly Asn Leu Met Gly Ser Tyr Arg Ser Val Gly Val Glu Thr Gly Glu
385                 390                 395                 400

Thr Lys Lys Glu Gly Ala Ala Arg Ser Gly Gly Gln Gly Gly Ile Arg
                405                 410                 415

Ala Arg Leu Arg Pro Ile Asp Ala Asp Thr Ile Asp Ile Tyr Ala Arg
            420                 425                 430

Ala Val Phe Pro Ala Ala Phe Ala Ala Val Asn Val Ile Tyr Trp Ala
        435                 440                 445

Ala Tyr Ala Met
    450

<210> SEQ ID NO 7
<211> LENGTH: 22
<212> TYPE: DNA
<213> ORGANISM: Homo sapiens

<400> SEQUENCE: 7
gcatgagtat acacgagtgt gc                                            22

<210> SEQ ID NO 8
<211> LENGTH: 22
<212> TYPE: DNA
<213> ORGANISM: Homo sapiens

<400> SEQUENCE: 8
gtaaagccgc acatcctagg ag                                            22

<210> SEQ ID NO 9
<211> LENGTH: 22
<212> TYPE: DNA
<213> ORGANISM: Homo sapiens

<400> SEQUENCE: 9
cagttagtct ccatctatgc ag                                            22

<210> SEQ ID NO 10
<211> LENGTH: 21
<212> TYPE: DNA
<213> ORGANISM: Homo sapiens

<400> SEQUENCE: 10
ccttgctctt gaactacact g                                             21

<210> SEQ ID NO 11
```

```
<211> LENGTH: 22
<212> TYPE: DNA
<213> ORGANISM: Homo sapiens

<400> SEQUENCE: 11
tatgcgtgct tggtgcatgt gc                                              22

<210> SEQ ID NO 12
<211> LENGTH: 23
<212> TYPE: DNA
<213> ORGANISM: Homo sapiens

<400> SEQUENCE: 12
ggatctggaa gactatcttt cac                                             23

<210> SEQ ID NO 13
<211> LENGTH: 22
<212> TYPE: DNA
<213> ORGANISM: Homo sapiens

<400> SEQUENCE: 13
gtgagacagt aacctcctca gc                                              22

<210> SEQ ID NO 14
<211> LENGTH: 22
<212> TYPE: DNA
<213> ORGANISM: Homo sapiens

<400> SEQUENCE: 14
gatagcatgc caaccctgat gc                                              22

<210> SEQ ID NO 15
<211> LENGTH: 22
<212> TYPE: DNA
<213> ORGANISM: Homo sapiens

<400> SEQUENCE: 15
cctggacttg gtggatttct tc                                              22

<210> SEQ ID NO 16
<211> LENGTH: 22
<212> TYPE: DNA
<213> ORGANISM: Homo sapiens

<400> SEQUENCE: 16
tcaccctaat cggagcaagc tg                                              22

<210> SEQ ID NO 17
<211> LENGTH: 22
<212> TYPE: DNA
<213> ORGANISM: Homo sapiens

<400> SEQUENCE: 17
tgccctttgg tccaagatcc tc                                              22

<210> SEQ ID NO 18
<211> LENGTH: 22
<212> TYPE: DNA
<213> ORGANISM: Homo sapiens

<400> SEQUENCE: 18
ctgtgtgaaa tgtggcgatt tc                                              22
```

```
<210> SEQ ID NO 19
<211> LENGTH: 20
<212> TYPE: DNA
<213> ORGANISM: Homo sapiens

<400> SEQUENCE: 19
gggattcagt tcaggttgtg                                          20

<210> SEQ ID NO 20
<211> LENGTH: 21
<212> TYPE: DNA
<213> ORGANISM: Homo sapiens

<400> SEQUENCE: 20
gggttggttc caagtctttg c                                        21

<210> SEQ ID NO 21
<211> LENGTH: 20
<212> TYPE: DNA
<213> ORGANISM: Homo sapiens

<400> SEQUENCE: 21
ccacttatac ctcctttccc                                          20

<210> SEQ ID NO 22
<211> LENGTH: 21
<212> TYPE: DNA
<213> ORGANISM: Homo sapiens

<400> SEQUENCE: 22
cgttatggcc tggctaaact c                                        21

<210> SEQ ID NO 23
<211> LENGTH: 22
<212> TYPE: DNA
<213> ORGANISM: Homo sapiens

<400> SEQUENCE: 23
catcacattg gtgacattgt gg                                       22

<210> SEQ ID NO 24
<211> LENGTH: 23
<212> TYPE: DNA
<213> ORGANISM: Homo sapiens

<400> SEQUENCE: 24
ccactactgt aaatagtcag ggc                                      23

<210> SEQ ID NO 25
<211> LENGTH: 22
<212> TYPE: DNA
<213> ORGANISM: Homo sapiens

<400> SEQUENCE: 25
gcctcttggt tgcagaagaa tc                                       22

<210> SEQ ID NO 26
<211> LENGTH: 21
<212> TYPE: DNA
<213> ORGANISM: Homo sapiens

<400> SEQUENCE: 26
cagtgaagga cctactagag g                                        21
```

```
<210> SEQ ID NO 27
<211> LENGTH: 22
<212> TYPE: DNA
<213> ORGANISM: Homo sapiens

<400> SEQUENCE: 27
tcaactctgg aagggtcact tg                                           22

<210> SEQ ID NO 28
<211> LENGTH: 22
<212> TYPE: DNA
<213> ORGANISM: Homo sapiens

<400> SEQUENCE: 28
acatctctcc atgagactca gt                                           22

<210> SEQ ID NO 29
<211> LENGTH: 22
<212> TYPE: DNA
<213> ORGANISM: Homo sapiens

<400> SEQUENCE: 29
tattgggtct cctacctcta cc                                           22

<210> SEQ ID NO 30
<211> LENGTH: 19
<212> TYPE: DNA
<213> ORGANISM: Homo sapiens

<400> SEQUENCE: 30
cagaacagtg ctgcatccc                                               19

<210> SEQ ID NO 31
<211> LENGTH: 18
<212> TYPE: DNA
<213> ORGANISM: Homo sapiens

<400> SEQUENCE: 31
cctagaggcc agcctaca                                                18

<210> SEQ ID NO 32
<211> LENGTH: 21
<212> TYPE: DNA
<213> ORGANISM: Homo sapiens

<400> SEQUENCE: 32
tcccatcgtg gctcccatgc t                                            21

<210> SEQ ID NO 33
<211> LENGTH: 21
<212> TYPE: DNA
<213> ORGANISM: Homo sapiens

<400> SEQUENCE: 33
tcatggtgta ctcctgtgga g                                            21

<210> SEQ ID NO 34
<211> LENGTH: 21
<212> TYPE: DNA
<213> ORGANISM: Homo sapiens

<400> SEQUENCE: 34
cacatctcag aggccaacat g                                            21
```

```
<210> SEQ ID NO 35
<211> LENGTH: 21
<212> TYPE: DNA
<213> ORGANISM: Homo sapiens

<400> SEQUENCE: 35
agccacagct tgtccacgaa g                                              21

<210> SEQ ID NO 36
<211> LENGTH: 21
<212> TYPE: DNA
<213> ORGANISM: Homo sapiens

<400> SEQUENCE: 36
ctacaaccac accaacgaga c                                              21

<210> SEQ ID NO 37
<211> LENGTH: 21
<212> TYPE: DNA
<213> ORGANISM: Homo sapiens

<400> SEQUENCE: 37
ttccaagcct tggagcgtcc a                                              21

<210> SEQ ID NO 38
<211> LENGTH: 20
<212> TYPE: DNA
<213> ORGANISM: Homo sapiens

<400> SEQUENCE: 38
aacacagtct gagaagtagc                                                20

<210> SEQ ID NO 39
<211> LENGTH: 19
<212> TYPE: DNA
<213> ORGANISM: Homo sapiens

<400> SEQUENCE: 39
gctttcctgc atcctgagc                                                 19

<210> SEQ ID NO 40
<211> LENGTH: 20
<212> TYPE: DNA
<213> ORGANISM: Homo sapiens

<400> SEQUENCE: 40
ccacctgtgt gcttttcctc                                                20

<210> SEQ ID NO 41
<211> LENGTH: 20
<212> TYPE: DNA
<213> ORGANISM: Homo sapiens

<400> SEQUENCE: 41
aagcatgaaa accacaggcg                                                20

<210> SEQ ID NO 42
<211> LENGTH: 20
<212> TYPE: DNA
<213> ORGANISM: Homo sapiens

<400> SEQUENCE: 42
```
tgagtcccat ggttgggctg                                              20

<210> SEQ ID NO 43
<211> LENGTH: 20
<212> TYPE: DNA
<213> ORGANISM: Homo sapiens

<400> SEQUENCE: 43
agggatgggg agtcctgttc                                              20

<210> SEQ ID NO 44
<211> LENGTH: 20
<212> TYPE: DNA
<213> ORGANISM: Homo sapiens

<400> SEQUENCE: 44
tacgacaatg gcaccacctg                                              20

<210> SEQ ID NO 45
<211> LENGTH: 18
<212> TYPE: DNA
<213> ORGANISM: Homo sapiens

<400> SEQUENCE: 45
cagtgctgtc cctggctc                                                18

<210> SEQ ID NO 46
<211> LENGTH: 20
<212> TYPE: DNA
<213> ORGANISM: Homo sapiens

<400> SEQUENCE: 46
atgggaacac ctgtggtcca                                              20

<210> SEQ ID NO 47
<211> LENGTH: 20
<212> TYPE: DNA
<213> ORGANISM: Homo sapiens

<400> SEQUENCE: 47
cttcttcgtc tcccctgtct                                              20

<210> SEQ ID NO 48
<211> LENGTH: 20
<212> TYPE: DNA
<213> ORGANISM: Homo sapiens

<400> SEQUENCE: 48
tgatgggctc ctacaggtcg                                              20

<210> SEQ ID NO 49
<211> LENGTH: 20
<212> TYPE: DNA
<213> ORGANISM: Homo sapiens

<400> SEQUENCE: 49
ttctcccagg aagtttctgg                                              20

<210> SEQ ID NO 50
<211> LENGTH: 41
<212> TYPE: DNA
<213> ORGANISM: Homo sapiens

<400> SEQUENCE: 50

```
ggatatgaca ataaacttca gcctgatata ggagtgaagc c                              41

<210> SEQ ID NO 51
<211> LENGTH: 33
<212> TYPE: DNA
<213> ORGANISM: Homo sapiens

<400> SEQUENCE: 51
gcgaattcat taaatggttg ctgatcttgg gcg                                       33
```

MUTATION ASSOCIATED WITH EPILEPSY

TECHNICAL FIELD

The present invention is concerned with a mutation associated with epilepsy.

BACKGROUND ART

Epilepsies constitute a diverse collection of brain disorders that affect about 3% of the population at some time in their lives (Annegers, 1996). An epileptic seizure can be defined as an episodic change in behaviour caused by the disordered firing of populations of neurons in the central nervous system. This results in varying degrees of involuntary muscle contraction and often a loss of consciousness. Epilepsy syndromes have been classified into more than 40 distinct types based upon characteristic symptoms, types of seizure, cause, age of onset and EEG patterns (Commission on Classification and Terminology of the International League Against Epilepsy, 1989). However the single feature that is common to all syndromes is the persistent increase in neuronal excitability that is both occasionally and unpredictably expressed as a seizure.

A genetic contribution to the aetiology of epilepsy has been estimated to be present in approximately 40% of affected individuals (Gardiner, 2000). As epileptic seizures may be the end-point of a number of molecular aberrations that ultimately disturb neuronal synchrony, the genetic basis for epilepsy is likely to be heterogeneous. There are over 200 Mendelian diseases which include epilepsy as part of the phenotype. In these diseases, seizures are symptomatic of underlying neurological involvement such as disturbances in brain structure or function. In contrast, there are also a number of "pure" epilepsy syndromes in which epilepsy is the sole manifestation in the affected individuals. These are termed idiopathic and account for over 60% of all epilepsy cases.

Idiopathic epilepsies have been further divided into partial and generalized sub-types. Partial (focal or local) epileptic fits arise from localized cortical discharges, so that only certain groups of muscles are involved and consciousness may be retained (Sutton, 1990). However, in generalized epilepsy, EEG discharge shows no focus such that all subcortical regions of the brain are involved. Although the observation that generalized epilepsies are frequently inherited is understandable, the mechanism by which genetic defects, presumably expressed constitutively in the brain, give rise to partial seizures is less clear.

The idiopathic generalized epilepsies (IGE) are the most common group of inherited human epilepsies. Two broad groups of IGE are now known—the classical idiopathic generalized epilepsies (Commission on Classification and Terminology of the International League Against Epilepsy, 1989) and the newly recognized genetic syndrome of generalized epilepsy with febrile seizures plus (GEFS$^+$) (Scheffer and Berkovic, 1997; Singh et al. 1999). The classical IGEs are divided into a number of clinically recognizable but overlapping sub-syndromes including childhood absence epilepsy (CAE), juvenile absence epilepsy, juvenile myoclonic epilepsy etc (Commission on Classification and Terminology of the International League Against Epilepsy, 1989; Roger et al. 1992). The sub-syndromes are identified by age of onset and the pattern of seizure types (absence, myoclonus and tonic-clonic). Some patients, particularly those with tonic-clonic seizures alone do not fit a specifically recognized sub-syndrome. Arguments for regarding these as separate syndromes, yet recognizing that they are part of a neurobiological continuum, have been presented previously (Berkovic et al. 1987; 1994; Reutens and Berkovic, 1995).

GEFS$^+$ was initially difficult to recognise as a distinct syndrome due to clinical heterogeneity within each affected family. Febrile seizures plus (FS$^+$) is a sub-syndrome where children have febrile seizures occurring outside the age range of 3 months to 6 years, or have associated febrile tonic-clonic seizures. Many family members have less common phenotypes which include FS$^+$ associated with absences, myoclonic or atonic seizures, while others have even more severe sub-syndromes such as myoclonic-astatic epilepsy.

Classical IGE and most GEFS$^+$ cases do not have simple Mendelian inheritance. This genetic heterogeneity, coupled with the phenotypic heterogeneity and incomplete penetrance, has impeded attempts to identify the genes involved. Despite this, the study of rare large families displaying primarily monogenic aetiology, has allowed the discovery of four genes causing two forms of IGE. In benign familial neonatal convulsions, mutations in the potassium channel genes, KCNQ2 and KCNQ3 have been identified (Charlier et al, 1998; Singh et al, 1998; Biervert et al, 1998), whereas in GEFS$^+$, mutations in the sodium channel genes SCN1A and SCN1B have been found (Wallace et al, 1998; 2001). However, mutations in these genes account for only a small percentage of the total IGE cases indicating that other genes are implicated.

Rodent models and human studies of absence epilepsies have often suggested abnormal GABAergic activity is involved (Destexhe, 1999; Vergnes et al, 2000; Feucht et al, 1999; Futatsugi et al, 1998). The involvement of the GABA-ergic system has also been implicated in other neuro/psychological disorders such as anxiety, manic depression, phobic obsessive symptoms, Alzheimer's disease, schizophrenia, migraine (Sibille et al., 2000; Gerner and Hare, 1981; Papadimitriou et al., 1998; Mizukami et al., 1998a; 1998b; Pearlson, 2000; Limmroth et al., 1996; Mitsikostas and Sanchez del Rio, 2001) and obesity (Blasi, 2000).

Gamma-Aminobutyric acid (GABA) is the most abundant inhibitory neurotransmitter in the central nervous system. GABA-ergic inhibition is mediated by two major classes of receptors, type A and type B. Type B receptors are members of the class of receptors coupled to G-proteins and mediate a variety of inhibitory effects via secondary messenger cascades. Type A receptors are ligand-gated chloride channels that mediate rapid inhibition. Unless the context requires otherwise, hereafter reference to a "GABA$_A$ receptor" should be construed as reference to a type A receptor.

Reduced levels of type A GABA, or GABA$_A$, receptors have been observed for some animal genetic models of generalised seizures, but the neurochemical differences have not been related to specific lesions leading to seizure susceptibility. These observations have been reviewed by Olsen et al. 1999 but all such disease models involve general observations concerning the presence or absence of a particular subunit of the GABA$_A$ receptors. There are approximately 16 separate, but related, genes which encode GABA$_A$ receptor subunits. These are grouped on the basis of sequence identity into α, β, γ, δ, ε and ρ subunits and there are six α subunits (designated α1, α2 etc), three β subunits, three γ subunits and three ρ subunits. Each GABA$_A$ receptor comprises five subunits which may each, at least in theory, be selected from any one of these subunits. The observations summarised by Olsen et al. 1999 show, for example, that mice in which the β3 subunit gene has been inactivated (knocked out) provide a suitable animal model for a human genetic disease, Angelman Syndrome, one symptom of which is epilepsy. Jackson et al. 1999 reports that there are many molecular variants of the $GABA_A$ receptor, and these variants have distinct pharmacologic properties. For example, the $GABA_A$ receptor γ subunit is not necessary for formation of a functional receptor, but when this subunit is omitted and receptors are expressed from α and β subunits alone, benzodiazepines are without effect. It is also to be noted that epileptic mice exhibit signs of anxiety and the benzodiazepines are anxiolytic drugs. However, there is no discussion of the mutations which may be responsible for defective $GABA_A$ receptors in humans in either article.

DISCLOSURE OF THE INVENTION

According to one aspect of the present invention there is provided an isolated mammalian DNA molecule encoding a mutant γ-aminobutyric acid type A ($GABA_A$) receptor subunit, wherein a mutation event selected from the group consisting of point mutations, deletions, insertions and rearrangements has occurred and said mutation event disrupts the functioning of an assembled $GABA_A$ receptor, or an otherwise functional fragment or homologue thereof. Typically a phenotype of epilepsy and/or anxiety and/or manic depression and/or phobic obsessive symptoms and/or Alzheimer's disease and/or schizophrenia and/or migraine and/or obesity is created. In particular, a phenotype of generalised epilepsy and more particularly childhood absence epilepsy, febrile seizures (including $FS^+$) and/or myoclonic epilepsy is created.

In a preferred form of the invention, the isolated mammalian DNA encodes a $GABA_A$ gamma subunit or a delta subunit.

In one embodiment of the present invention there is provided an isolated, mammalian DNA encoding a mutant $GABA_A$ gamma-2 subunit in which a mutation event selected from the group consisting of point mutations, deletions, insertions and rearrangements has occurred in the nucleotides encoding an extracellular region of the $GABA_A$ gamma subunit, wherein said mutation event abolishes or reduces diazepam potentiation of the GABA response, or an otherwise functional fragment or homologue thereof.

Typically said mutation event occurs in the nucleotides encoding a benzodiazepine binding domain, specifically in the large extracellular loop of the $GABA_A$ gamma subunit. Typically, said mutation event is a point mutation.

In one form of the invention, the mutation is in exon 2 and results in replacement of a highly conserved arginine, typically with a glutamine residue, at residue 43 (R43Q) of the mature gamma-2 subunit of the $GABA_A$ receptor, which is residue 82 of the precursor protein. The R43Q mutation occurs as a result of a G to A nucleotide substitution at position 471 (c245) of the gamma-2 subunit of the $GABA_A$ receptor as shown in SEQ ID NO:1.

Without wishing to be bound by theory it is speculated that the mutation serves to inhibit binding of endogenous benzodiazepine-like compounds (endozepines) to said receptor.

In a further embodiment of the present invention, there is provided an isolated mammalian DNA encoding a mutant $GABA_A$ gamma-2 subunit in which a mutation event selected from the group consisting of point mutations, deletions, insertions and rearrangements has occurred in the nucleotides encoding the large cytoplasmic loop between the third and fourth transmembrane domains of the protein, or an otherwise functional fragment or homologue thereof.

Typically said mutation event is a point mutation. In one form of the invention the mutation is in exon 9 and typically results in the replacement of a highly conserved glutamine residue with a stop codon at position 351 (Q351X) of the mature protein. The Q351X mutation occurs as a result of a C to T nucleotide substitution at position 1394 (c1168) of the gamma-2 subunit of the $GABA_A$ receptor as shown in SEQ ID NO:2.

Said mutation gives rise to a truncated protein missing the fourth membrane spanning domain which leads to the formation of a non-functional $GABA_A$ receptor complex that has a dominant-negative effect over wild-type receptor complexes.

Without wishing to be bound by theory, this dominant-negative effect is most likely due to a reduction in the density of functional $GABA_A$ receptors leading to decreased inhibitory responses to GABA, thereby increasing neuronal excitability and seizures.

In a still further embodiment of the present invention, there is provided an isolated mammalian DNA encoding a mutant $GABA_A$ delta subunit, in which a mutation event selected from the group consisting of point mutations, deletions, insertions and rearrangements has occurred in the nucleotides encoding the large extracellular domain, or an otherwise functional fragment or homologue thereof.

Typically said mutation is a point mutation. In one form of the invention the mutation typically results in the replacement of an arginine residue with a cysteine at position 172 (R172C) of the mature delta subunit protein which is residue 220 of the precursor protein. The R172C mutation occurs as a result of a C to T nucleotide substitution (c658) in the delta subunit of the $GABA_A$ receptor as shown in SEQ ID NO:3.

Without wishing to be bound by theory it is speculated that the mutation introduces a cysteine residue into the protein which may compete for disulphide bond formation with the cysteine residues that initiate disulphide bond formation in the wild-type protein. Abnormal bond formation may serve to disturb the correct tertiary structure formation of the protein so as to disrupt the functioning of the receptor.

The present invention also encompasses DNA molecules in which one or more additional mutation events selected from the group consisting of point mutations, deletions, insertions and rearrangements have occurred. Any such DNA molecule will have the mutation described above but would otherwise be functional. As will be well understood by the person skilled in the art, such molecules may vary significantly from the DNA molecules set forth in SEQ ID NO:1–3.

The nucleotide sequences of the present invention can be engineered using methods accepted in the art for a variety of purposes. These include, but are not limited to, modification of the cloning, processing, and/or expression of the gene product. PCR reassembly of gene fragments and the use of synthetic oligonucleotides allow the engineering of the nucleotide sequences of the present invention. For example, oligonucleotide-mediated site-directed mutagenesis can introduce further mutations that create new restriction sites, alter expression patterns and produce splice variants etc.

As a result of the degeneracy of the genetic code, a number of polynucleotide sequences, some that may have minimal similarity to the polynucleotide sequences of any known and naturally occurring gene, may be produced. Thus, the invention includes each and every possible variation of a polynucleotide sequence that could be made by selecting combinations based on possible codon choices. These combinations are made in accordance with the standard triplet genetic code as applied to the polynucleotide sequences of the present invention, and all such variations are to be considered as being specifically disclosed.

The DNA molecules of this invention include cDNA, genomic DNA, synthetic forms, and mixed polymers, both sense and antisense strands, and may be chemically or biochemically modified, or may contain non-natural or derivatised nucleotide bases as will be appreciated by those skilled in the art. Such modifications include labels, methylation, intercalators, alkylators and modified linkages. In some instances it may be advantageous to produce nucleotide sequences possessing a substantially different codon usage than that of the polynucleotide sequences of the present invention. For example, codons may be selected to increase the rate of expression of the peptide in a particular prokaryotic or eukaryotic host corresponding with the frequency that particular codons are utilized by the host. Other reasons to alter the nucleotide sequence without altering the encoded amino acid sequences include the production of RNA transcripts having more desirable properties, such as a greater half-life, than transcripts produced from the naturally occurring mutated sequence.

The invention also encompasses production of DNA sequences of the present invention entirely by synthetic chemistry. Synthetic sequences may be inserted into expression vectors and cell systems that contain the necessary elements for transcriptional and translational control of the inserted coding sequence in a suitable host. These elements may include regulatory sequences, promoters, 5' and 5' untranslated regions and specific initiation signals (such as an ATG initiation codon and Kozak consensus sequence) which allow more efficient translation of sequences encoding the polypeptides of the present invention. In cases where the complete coding sequence, including the initiation codon and upstream regulatory sequences, are inserted into the appropriate expression vector, additional control signals may not be needed. However, in cases where only coding sequence, or a fragment thereof, is inserted, exogenous translational control signals as described above should be provided by the vector. Such signals may be of various origins, both natural and synthetic. The efficiency of expression may be enhanced by the inclusion of enhancers appropriate for the particular host cell system used (Scharf et al., 1994).

The invention also includes nucleic acid molecules that are the complements of the sequences described herein.

According to another aspect of the present invention there is provided an isolated DNA molecule comprising the nucleotide sequence set forth in any one of SEQ ID NOS:1–3.

According to still another aspect of the present invention there is provided an isolated DNA molecule consisting of the nucleotide sequence set forth in any one of SEQ ID NOS: 1–3.

The present invention allows for the preparation of purified polypeptide or protein from the polynucleotides of the present invention, or variants thereof. In order to do this, host cells may be transformed with a DNA molecule as described above. Typically said host cells are transfected with an expression vector comprising a DNA molecule according to the invention. A variety of expression vector/host systems may be utilized to contain and express sequences encoding polypeptides of the invention. These include, but are not limited to, microorganisms such as bacteria transformed with plasmid or cosmid DNA expression vectors; yeast transformed with yeast expression vectors; insect cell systems infected with viral expression vectors (e.g., baculovirus); or mouse or other animal or human tissue cell systems. Mammalian cells can also be used to express a protein using a vaccinia virus expression system. The invention is not limited by the host cell or vector employed.

The polynucleotide sequences, or variants thereof, of the present invention can be stably expressed in cell lines to allow long term production of recombinant proteins in mammalian systems. Sequences encoding the polypeptides of the present invention can be transformed into cell lines using expression vectors which may contain viral origins of replication and/or endogenous expression elements and a selectable marker gene on the same or on a separate vector. The selectable marker confers resistance to a selective agent, and its presence allows growth and recovery of cells which successfully express the introduced sequences. Resistant clones of stably transformed cells may be propagated using tissue culture techniques appropriate to the cell type.

In addition, a host cell strain may be chosen for its ability to modulate expression of the inserted sequences or to process the expressed protein in the desired fashion. Such modifications of the polypeptide include, but are not limited to, acetylation, glycosylation, phosphorylation, and acylation. Post-translational cleavage of a "prepro" form of the protein may also be used to specify protein targeting, folding, and/or activity. Different host cells having specific cellular machinery and characteristic mechanisms for post-translational activities (e.g., CHO or HeLa cells), are available from the American Type Culture Collection (ATCC) and may be chosen to ensure the correct modification and processing of the foreign protein.

When large quantities of the protein product of the gene are needed, such as for antibody production, vectors which direct high levels of expression of this protein may be used, such as those containing the T5 or T7 inducible bacteriophage promoter. The present invention also includes the use of the expression systems described above in generating and isolating fusion proteins which contain important functional domains of the protein. These fusion proteins are used for binding, structural and functional studies as well as for the generation of appropriate antibodies.

In order to express and purify the protein as a fusion protein, the appropriate cDNA sequence is inserted into a vector which contains a nucleotide sequence encoding another peptide (for example, glutathionine succinyl transferase). The fusion protein is expressed and recovered from prokaryotic or eukaryotic cells. The fusion protein can then be purified by affinity chromatography based upon the fusion vector sequence. The desired protein is then obtained by enzymatic cleavage of the fusion protein.

Fragments of the polypeptides of the present invention may also be produced by direct peptide synthesis using solid-phase techniques. Automated synthesis may be achieved by using the ABI 431A Peptide Synthesizer (Perkin-Elmer). Various fragments of this protein may be synthesized separately and then combined to produce the full length molecule.

According to another aspect of the present invention there is provided an isolated mammalian polypeptide, said polypeptide being a mutant γ-aminobutyric acid type A (GABA$_A$) receptor subunit, wherein a mutation event selected from the group consisting of substitutions, deletions, truncations, insertions and rearrangements has occurred and said mutation event disrupts the functioning of an assembled GABA$_A$ receptor, or an otherwise functional fragment or homologue thereof. Typically a phenotype of epilepsy and/or anxiety and/or manic depression and/or phobic obsessive symptoms and/or Alzheimer's disease and/ or schizophrenia and/or migraine and/or obesity is created. In particular, a phenotype of generalised epilepsy and more particularly childhood absence epilepsy, febrile seizures (including FS+) and/or myoclonic epilepsy is created.

In a preferred form of the invention the polypeptide is a mutant gamma-2 or delta subunit of a mammalian GABA$_A$ receptor.

In one embodiment of the present invention there is provided a mutant GABA$_A$ gamma-2 subunit, in which a mutation event selected from the group consisting of point mutations, deletions, truncations, insertions and rearrangements has occurred in an extracellular region of the GABA$_A$ gamma-2 subunit, wherein said mutation abolishes or reduces diazepam potentiation of the GABA response, or an otherwise functional fragment or homologue thereof.

Typically the mutation is in a benzodiazepine binding domain, specifically in the large extracellular loop of the GABA$_A$ gamma-2 subunit.

Typically the mutation is a point mutation.

In one form of the invention the mutation event is a substitution in which an arginine residue is replaced with a glutamine residue in the large extracellular domain of the gamma-2 subunit protein in a benzodiazepine binding site. Preferably the substitution is an R43Q transition as illustrated in SEQ ID NO:4 (precursor protein sequence is listed).

In a further embodiment of the present invention there is provided a mutant GABA$_A$ gamma-2 subunit in which a mutation event selected from the group consisting of point mutations, deletions, truncations, insertions and rearrangements has occurred in the large cytoplasmic loop between the third and fourth transmembrane domains of the protein, or an otherwise functional fragment or homologue thereof.

In a further form of the invention the mutation event involves substitution of a codon for a glutamine residue with a stop codon in the large cytoplasmic loop between the third and fourth membrane spanning domain of the gamma-2 subunit protein. Preferably the substitution is a Q351X transition as illustrated in SEQ ID NO:5 (precursor protein sequence is listed).

In a still further embodiment of the present invention there is provided a mutant GABA$_A$ delta subunit in which a mutation event selected from the group consisting of point mutations, deletions, truncations, insertions and rearrangements has occurred, or an otherwise functional fragment or homologue thereof.

In a still further form of the invention the mutation event is a substitution involving an arginine residue replaced with a cysteine residue in the large extracellular domain of the delta subunit protein. Preferably the substitution is an R172C transition as illustrated in SEQ ID NO:6 (precursor protein sequence is listed).

The isolated polypeptides of the present invention may have been subjected to one or more mutation events selected from the group consisting of substitutions, deletions, truncations, insertions and rearrangements in addition to the mutation associated with epilepsy. Typically these mutation events are conservative substitutions.

According to still another aspect of the present invention there is provided an isolated polypeptide comprising the sequence set forth in any one of SEQ ID NOS:4–6.

According to still another aspect of the present invention there is provided a polypeptide consisting of the amino acid sequence set forth in any one of SEQ ID NOS:4–6.

According to still another aspect of the present invention there is provided an isolated polypeptide complex, said polypeptide complex being an assembled mammalian GABA$_A$ receptor, wherein a mutation event selected from the group consisting of substitutions, deletions, truncations, insertions and rearrangements has occurred in a subunit thereof, and said mutation event disrupts the functioning of the assembled GABA$_A$ receptor so as, typically, to produce a phenotype of epilepsy and/or anxiety and/or manic depression and/or phobic obsessive symptoms and/or Alzheimer's disease and/or schizophrenia and/or migraine and/or obesity, or an otherwise functional fragment or homologue thereof. In particular, a phenotype of generalised epilepsy and more particularly childhood absence epilepsy, febrile seizures (including FS+) and/or myoclonic epilepsy is created.

According to still another aspect of the present invention there is provided a method of preparing a polypeptide, said polypeptide being a mutant GABA$_A$ receptor subunit, comprising the steps of:

(1) culturing host cells transfected with an expression vector comprising a DNA molecule as described above under conditions effective for polypeptide production; and (2) harvesting the mutant GABA$_A$ receptor subunit.

The mutant GABA$_A$ receptor subunit may be allowed to assemble with other subunits of the GABA$_A$ receptor that are either wild-type or themselves mutant subunits, whereby the assembled GABA$_A$ receptor is harvested.

Substantially purified protein or fragments thereof can then be used in further biochemical analyses to establish secondary and tertiary structure for example by X-ray crystallography of crystals of the proteins or of the assembled GABA receptor or by nuclear magnetic resonance (NMR). Determination of structure allows for the rational design of pharmaceuticals to interact with the GABA$_A$ receptor as a whole or through interaction with a specific subunit protein, alter the overall GABA receptor protein charge configuration or charge interaction with other proteins, or to alter its function in the cell.

It will be appreciated that, having identified a mutation involved in epilepsy in the GABA$_A$ receptor subunit proteins, the GABA$_A$ receptors and associated subunits will be useful in further applications which include a variety of hybridisation and immunological assays to screen for and detect the presence of either a normal or mutated gene or gene product.

Expression of the mutant GABA$_A$ receptor subunits of the present invention creates a phenotype of epilepsy, in particular childhood absence epilepsy, febrile seizures (including FS+) and myoclonic epilepsy and/or anxiety and/or manic depression and/or phobic obsessive symptoms and/or Alzheimer's disease and/or schizophrenia and/or migraine and/or obesity. It will be appreciated that this phenotype may present with other symptoms and/or conditions and therefore the invention enables therapeutic methods for the treatment of disorders including, but not restricted to, epilepsy, in particular childhood absence epilepsy, febrile seizures (including FS+) and myoclonic epilepsy and/or anxiety and/or manic depression and/or phobic obsessive symptoms and/or Alzheimer's disease and/or schizophrenia and/or migraine and/or obesity. The invention also enables methods for the diagnosis of disorders including, but not restricted to, epilepsy, in particular childhood absence epilepsy, febrile seizures (including FS+) and myoclonic epilepsy and/or anxiety and/or manic depression and/or phobic obsessive symptoms and/or Alzheimer's disease and/or schizophrenia and/or migraine and/or obesity.

According to still another aspect of the invention there is provided a method of treating epilepsy, in particular childhood absence epilepsy, febrile seizures (including FS+) and myoclonic epilepsy and/or anxiety and/or manic depression and/or phobic obsessive symptoms and/or Alzheimer's disease and/or schizophrenia and/or migraine and/or obesity, comprising administering a wild-type $GABA_A$ receptor polypeptide or receptor subunit polypeptide as described above, or an agonist or modulator of the $GABA_A$ receptor, when the $GABA_A$ receptor contains a mutation in any one of the subunits comprising the receptor, said mutation being causative of the disorder, to a subject in need of such treatment.

In still another aspect of the invention there is provided the use of a selective agonist or modulator of the $GABA_A$ receptor when the receptor contains a mutation in any one of the subunits comprising the receptor, said mutation being causative of a disorder including, but not restricted to, epilepsy, in particular childhood absence epilepsy, febrile seizures (including FS+) and myoclonic epilepsy and/or anxiety and/or manic depression and/or phobic obsessive symptoms and/or Alzheimer's disease and/or schizophrenia and/or migraine and/or obesity, in the manufacture of a medicament for the treatment of the disorder.

In one aspect of the invention, a suitable agonist or modulator will be able to restore diazepam potentiation of the GABA response in mutant $GABA_A$ receptors when the mutation occurs in a benzodiazepine binding site of the gamma-2 subunit.

In another aspect of the present invention, a suitable agonist or modulator may allow efficient incorporation of $GABA_A$ receptors containing truncated gamma-2 subunits into the cell membrane so as to restore receptor function.

Alternatively, a suitable agonist or modulator may be chosen that is able to increase the response to GABA in the remaining functional receptors.

Proteins or peptides which represent an appropriate $GABA_A$ receptor subunit can be supplied to cells which contain the corresponding mutant or missing GABA receptor subunit. $GABA_A$ receptor subunit protein can be produced as described above and can be introduced into cells by microinjection or by use of liposomes as another example. Some molecules may be taken up by cells actively or by diffusion. Supply of proteins or peptides with the appropriate $GABA_A$ receptor subunit activity to cells deficient in such subunits should lead to partial reversal of epilepsy, in particular childhood absence epilepsy, febrile seizures (including FS+) and myoclonic epilepsy and/or anxiety and/or manic depression and/or phobic obsessive symptoms and/or Alzheimer's disease and/or schizophrenia and/or migraine and/or obesity, in the manufacture of a medicament for the treatment of the disorder.

Other molecules with $GABA_A$ receptor subunit activity (for example drugs or organic compounds) may also be used for therapy.

A pharmaceutical composition comprising substantially purified $GABA_A$ receptor subunit, typically a $GABA_A$ gamma or delta subunit, and a pharmaceutically acceptable carrier may be administered.

Pharmaceutical compositions in accordance with the present invention are prepared by mixing the appropriate $GABA_A$ receptor subunit or active fragments or variants thereof having the desired degree of purity, with acceptable carriers, excipients, or stabilizers which are well known. Acceptable carriers, excipients or stabilizers are nontoxic at the dosages and concentrations employed, and include buffers such as phosphate, citrate, and other organic acids; antioxidants including absorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitrol or sorbitol; salt-forming counterions such as sodium; and/or nonionic surfactants such as Tween, Pluronics or polyethylene glycol (PEG).

The appropriate $GABA_A$ receptor subunit gene or fragment thereof may be employed in gene therapy methods to increase the level of expression of the gene in those persons in which the mutant gene is expressed but the gene product is non-functional.

Alternatively, the appropriate $GABA_A$ receptor subunit gene, or fragments thereof, may be delivered to affected cells in a form in which it can be taken up and can code for sufficient protein to provide effective function. Alternatively, in some mutants, it may be possible to prevent disease by introducing another copy of the homologous gene bearing a second mutation in that gene, or to alter the mutation, or to use another gene to block any negative effect.

According to still another aspect of the present invention there is provided a method of treating epilepsy and/or anxiety and/or manic depression and/or phobic obsessive symptoms and/or Alzheimer's disease and/or schizophrenia and/or migraine and/or obesity, comprising administering an agonist or modulator of the GABA receptor and/or an isolated DNA molecule as described above or a wild-type $GABA_A$ receptor or $GABA_A$ receptor subunit to a subject in need of such treatment.

In a further aspect there is provided the use of an agonist or modulator of the $GABA_A$ receptor and/or isolated DNA molecule as described above or a wild-type GABA receptor or $GABA_A$ receptor subunit in the manufacture of a medicament for the treatment of epilepsy and/or anxiety and/or manic depression and/or phobic obsessive symptoms and/or Alzheimer's disease and/or schizophrenia and/or migraine and/or obesity.

Typically, a vector capable of expressing the appropriate $GABA_A$ receptor subunit or a fragment or derivative thereof may be administered to a subject such that the gene will be expressed by the cell and remain extrachromosomal or ideally will be introduced into the cell such that it recombines with the endogenous mutant gene present in the cell. This requires a double recombination event for the correction of the gene mutation. Vectors for the introduction of genes in these ways are known in the art, and any suitable vector may be used.

Appropriate vectors for gene therapy include plasmid vectors and virus vectors including transducing retroviral vectors, adenoviruses, adeno-associated virus, vaccinia virus, papovaviruses, lentiviruses and retroviruses of avian, murine and human origin.

Gene therapy would be carried out according to accepted methods (Friedman, 1991; Culver, 1996). A vector containing a copy of the appropriate GABA receptor subunit gene linked to expression control elements and capable of replicating inside the cells is prepared. Alternatively the vector may be replication deficient and may require helper cells for replication and use in gene therapy. The vector is then injected into the patient and if the gene is not permanently incorporated into the genome of the target cells, the treatment may have to be repeated.

Gene transfer using non-viral methods of infection in vitro can also be used. These methods include direct injection of DNA, uptake of naked DNA in the presence of calcium phosphate, electroporation, protoplast fusion or liposome delivery. Gene transfer can also be achieved by delivery as a part of a human artificial chromosome or receptor-mediated gene transfer. This involves linking the DNA to a targeting molecule that will bind to specific cell-surface receptors to induce endocytosis and transfer of the DNA into mammalian cells. One such technique uses poly-L-lysine to link asialoglycoprotein to DNA. An adenovirus is also added to the complex to disrupt the lysosomes and thus allow the DNA to avoid degradation and move to the nucleus. Infusion of these particles intravenously has resulted in gene transfer into hepatocytes.

Gene transfer techniques which target DNA directly to the brain are preferred. For example, patients carrying a $GABA_A$ receptor subunit susceptible allele are treated with a gene delivery method such that some or all of their brain precursor cells receive at least one additional functional normal copy of the appropriate $GABA_A$ receptor subunit needed. The treated individuals should have a reduced risk of disease due to the fact that the susceptible allele has been countered by the presence of the normal allele.

According to still another aspect of the invention there is provided a method of treating epilepsy and/or anxiety and/or manic depression and/or phobic obsessive symptoms and/or Alzheimer's disease and/or schizophrenia and/or migraine and/or obesity, comprising administering a selective antagonist or modulator of the $GABA_A$ receptor or receptor subunit, when the receptor contains a mutation in a subunit comprising the receptor, said mutation being causative of the disorder, to a subject in need of such treatment.

In still another aspect of the invention there is provided the use of a selective antagonist or modulator of the $GABA_A$ receptor when the receptor contains a mutation in a subunit comprising the receptor, said mutation being causative of epilepsy and/or anxiety and/or manic depression and/or phobic obsessive symptoms and/or Alzheimer's disease and/or schizophrenia and/or migraine and/or obesity, in the manufacture of a medicament for the treatment of the disorder.

Using methods well known in the art, a mutant $GABA_A$ receptor may be used to produce antibodies specific for the mutant receptor that is causative of the disease or to screen libraries of pharmaceutical agents to identify those that specifically bind the mutant GABA receptor.

In one aspect, an antibody, which specifically binds to a mutant $GABA_A$ receptor, may be used directly as an antagonist or modulator, or indirectly as a targeting or delivery mechanism for bringing a pharmaceutical agent to cells or tissues that express the mutant GABA receptor.

In a still further aspect of the invention there is provided an antibody which is immunologically reactive with a polypeptide as described above, but not with a wild-type $GABA_A$ receptor or subunit thereof.

In particular, there is provided an antibody to an assembled $GABA_A$ receptor containing a mutation causative of a disorder, as described above, in a subunit comprising the receptor. Such antibodies may include, but are not limited to, polyclonal, monoclonal, chimeric, and single chain antibodies as would be understood by the person skilled in the art.

For the production of antibodies, various hosts including rabbits, rats, goats, mice, humans, and others may be immunized by injection with a polypeptide as described or with any fragment or oligopeptide thereof which has immunogenic properties. Various adjuvants may be used to increase immunological response and include, but are not limited to, Freund's, mineral gels such as aluminum hydroxide, and surface-active substances such as lysolecithin. Adjuvants used in humans include BCG (bacilli Calmette-Guerin) and *Corynebacterium parvum*.

It is preferred that the oligopeptides, peptides, or fragments used to induce antibodies to the mutant GABA receptor have an amino acid sequence consisting of at least 5 amino acids, and, more preferably, of at least 10 amino acids. It is also preferable that these oligopeptides, peptides, or fragments are identical to a portion of the amino acid sequence of the natural protein and contain the entire amino acid sequence of a small, naturally occurring molecule. Short stretches of $GABA_A$ receptor amino acids may be fused with those of another protein, such as KLH, and antibodies to the chimeric molecule may be produced.

Monoclonal antibodies to a mutant $GABA_A$ receptor may be prepared using any technique which provides for the production of antibody molecules by continuous cell lines in culture. These include, but are not limited to, the hybridoma technique, the human B-cell hybridoma technique, and the EBV-hybridoma technique. (For example, see Kohler et al., 1975; Kozbor et al., 1985; Cote et al., 1983; Cole et al., 1984).

Antibodies may also be produced by inducing in vivo production in the lymphocyte population or by screening immunoglobulin libraries or panels of highly specific binding reagents as disclosed in the literature. (For example, see Orlandi et al., 1989; Winter et al., 1991).

Antibody fragments which contain specific binding sites for a $GABA_A$ receptor may also be generated. For example, such fragments include, F(ab')2 fragments produced by pepsin digestion of the antibody molecule and Fab fragments generated by reducing the disulfide bridges of the F(ab')2 fragments. Alternatively, Fab expression libraries may be constructed to allow rapid and easy identification of monoclonal Fab fragments with the desired specificity. (For example, see Huse et al., 1989).

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between a $GABA_A$ receptor and its specific antibody. A two-site, monoclonal-based immunoassay utilizing monoclonal antibodies reactive to two non-interfering $GABA_A$ receptor epitopes is preferred, but a competitive binding assay may also be employed.

In a further aspect of the invention there is provided a method of treating epilepsy and/or anxiety and/or manic depression and/or phobic obsessive symptoms and/or Alzheimer's disease and/or schizophrenia and/or migraine and/or obesity, comprising administering an isolated DNA molecule which is the complement (antisense) of any one of the DNA molecules described above and which encodes a mRNA that hybridizes with the mRNA encoding a mutant $GABA_A$ receptor subunit, to a subject in need of such treatment.

In a still further aspect of the invention there is provided the use of an isolated DNA molecule which is the complement of a DNA molecule of the invention and which encodes a mRNA that hybridizes with the mRNA encoding a mutant $GABA_A$ receptor subunit, in the manufacture of a medicament for the treatment of epilepsy and/or anxiety and/or manic depression and/or phobic obsessive symptoms and/or Alzheimer's disease and/or schizophrenia and/or migraine and/or obesity.

Typically, a vector expressing the complement of the polynucleotide encoding the subunits constituting the $GABA_A$ receptor may be administered to a subject in need of such treatment. Antisense strategies may use a variety of approaches including the use of antisense oligonucleotides, injection of antisense RNA and transfection of antisense RNA expression vectors. Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection, by liposome injections, or by polycationic amino polymers may be achieved using methods which are well known in the art. (For example, see Goldman et al., 1997).

In further embodiments, any of the agonists, proteins, antagonists, modulators, antibodies, complementary sequences or vectors of the invention may be administered in combination with other appropriate therapeutic agents. Selection of the appropriate agents may be made by those skilled in the art, according to conventional pharmaceutical principles. The combination of therapeutic agents may act synergistically to effect the treatment or prevention of the various disorders described above. Using this approach, therapeutic efficacy with lower dosages of each agent may be possible, thus reducing the potential for adverse side effects.

According to still another aspect of the invention, peptides of the invention, particularly purified mutant $GABA_A$ receptor polypeptide and cells expressing these, are useful for the screening of candidate pharmaceutical agents in a variety of techniques. It will be appreciated that therapeutic agents useful in the treatment of epilepsy and/or anxiety and/or manic depression and/or phobic obsessive symptoms and/or Alzheimer's disease and/or schizophrenia and/or migraine and/or obesity are likely to show binding affinity to the polypeptides of the invention. Such techniques include, but are not limited to, utilising eukaryotic or prokaryotic host cells that are stably transformed with recombinant polypeptides expressing the polypeptide or fragment, preferably in competitive binding assays. Binding assays will measure for the formation of complexes between a specific GABA receptor subunit polypeptide or fragment and the agent being tested, or will measure the degree to which an agent being tested will interfere with the formation of a complex between a specific $GABA_A$ receptor subunit polypeptide or fragment and a known ligand.

Another technique for drug screening provides high-throughput screening for compounds having suitable binding affinity to the mutant $GABA_A$ receptor polypeptides (see PCT published application WO84/03564). In this stated technique, large numbers of small peptide test compounds can be synthesised on a solid substrate and can be assayed through $GABA_A$ receptor polypeptide binding and washing. Bound $GABA_A$ receptor polypeptide is then detected by methods well known in the art. In a variation of this technique, purified polypeptides of the invention can be coated directly onto plates to identify interacting test compounds.

The invention also contemplates the use of competition drug screening assays in which neutralizing antibodies capable of specifically binding the mutant GABA receptor compete with a test compound for binding thereto. In this manner, the antibodies can be used to detect the presence of any peptide that shares one or more antigenic determinants of the mutant $GABA_A$ receptor.

The invention is particularly useful for screening compounds by using the polypeptides of the invention in transformed cells, transfected or injected oocytes or transgenic animals. A particular drug is added to the cells in culture or administered to a transgenic animal containing the mutant $GABA_A$ receptor and the effect on the current of the receptor is compared to the current of a cell or animal containing the wild-type $GABA_A$ receptor. Drug candidates that alter the current to a more normal level are useful for treating or preventing epilepsy and/or anxiety and/or manic depression and/or phobic obsessive symptoms and/or Alzheimer's disease and/or schizophrenia and/or migraine and/or obesity.

The polypeptides of the present invention may also be used for screening compounds developed as a result of combinatorial library technology. This provides a way to test a large number of different substances for their ability to modulate activity of a polypeptide. The use of peptide libraries is preferred (see WO 97/02048) with such libraries and their use known in the art.

A substance identified as a modulator of polypeptide function may be peptide or non-peptide in nature. Non-peptide "small molecules" are often preferred for many in vivo pharmaceutical applications. In addition, a mimic or mimetic of the substance may be designed for pharmaceutical use. The design of mimetics based on a known pharmaceutically active compound ("lead" compound) is a common approach to the development of novel pharmaceuticals. This is often desirable where the original active compound is difficult or expensive to synthesise or where it provides an unsuitable method of administration. In the design of a mimetic, particular parts of the original active compound that are important in determining the target property are identified. These parts or residues constituting the active region of the compound are known as its pharmacophore. Once found, the pharmacophore structure is modelled according to its physical properties using data from a range of sources including x-ray diffraction data and NMR. A template molecule is then selected onto which chemical groups which mimic the pharmacophore can be added. The selection can be made such that the mimetic is easy to synthesise, is likely to be pharmacologically acceptable, does not degrade in vivo and retains the biological activity of the lead compound. Further optimisation or modification can be carried out to select one or more final mimetics useful for in vivo or clinical testing.

It is also possible to isolate a target-specific antibody and then solve its crystal structure. In principle, this approach yields a pharmacophore upon which subsequent drug design can be based as described above. It may be possible to avoid protein crystallography altogether by generating anti-idiotypic antibodies (anti-ids) to a functional, pharmacologically active antibody. As a mirror image of a mirror image, the binding site of the anti-ids would be expected to be an analogue of the original receptor. The anti-id could then be used to isolate peptides from chemically or biologically produced peptide banks.

Any of the therapeutic methods described above may be applied to any subject in need of such therapy, including, for example, mammals such as dogs, cats, cows, horses, rabbits, monkeys, and most preferably, humans.

Polynucleotide sequences encoding a $GABA_A$ receptor subunit may be used for the diagnosis of epilepsy, in particular childhood absence epilepsy, febrile seizures (including FS$^+$) and myoclonic epilepsy and/or anxiety and/or manic depression and/or phobic obsessive symptoms and/or Alzheimer's disease and/or schizophrenia and/or migraine and/or obesity and the use of the DNA molecules of the invention in diagnosis of these disorders, or a predisposition to these disorders, is therefore contemplated.

In another embodiment of the invention, the polynucleotides that may be used for diagnostic purposes include oligonucleotide sequences, genomic DNA and complementary RNA and DNA molecules. The polynucleotides may be used to detect and quantitate gene expression in biological samples. Genomic DNA used for the diagnosis may be obtained from body cells, such as those present in the blood, tissue biopsy, surgical specimen, or autopsy material. The DNA may be isolated and used directly for detection of a specific sequence or may be amplified by the polymerase chain reaction (PCR) prior to analysis. Similarly, RNA or cDNA may also be used, with or without PCR amplification. To detect a specific nucleic acid sequence, hybridisation using specific oligonucleotides, restriction enzyme digest and mapping, PCR mapping, RNAse protection, and various other methods may be employed. For instance direct nucleotide sequencing of amplification products from the GABA receptor subunits can be employed. Sequence of the sample amplicon is compared to that of the wild-type amplicon to determine the presence (or absence) of nucleotide differences.

According to a further aspect of the invention there is provided the use of a polypeptide as described above in the diagnosis of epilepsy and/or anxiety and/or manic depression and/or phobic obsessive symptoms and/or Alzheimer's disease and/or schizophrenia and/or migraine and/or obesity.

When a diagnostic assay is to be based upon proteins constituting a $GABA_A$ receptor, a variety of approaches are possible. For example, diagnosis can be achieved by monitoring differences in the electrophoretic mobility of normal and mutant proteins that form the $GABA_A$ receptor. Such an approach will be particularly useful in identifying mutants in which charge substitutions are present, or in which insertions, deletions or substitutions have resulted in a significant change in the electrophoretic migration of the resultant protein. Alternatively, diagnosis may be based upon differences in the proteolytic cleavage patterns of normal and mutant proteins, differences in molar ratios of the various amino acid residues, or by functional assays demonstrating altered function of the gene products.

In another aspect, antibodies that specifically bind mutant $GABA_A$ receptors may be used for the diagnosis of epilepsy, or in assays to monitor patients being treated with a complete $GABA_A$ receptor or agonists, antagonists, modulators or inhibitors of a $GABA_A$ receptor. Antibodies useful for diagnostic purposes may be prepared in the same manner as described above for therapeutics. Diagnostic assays for $GABA_A$ receptors include methods that utilize the antibody and a label to detect a mutant $GABA_A$ receptor in human body fluids or in extracts of cells or tissues. The antibodies may be used with or without modification, and may be labelled by covalent or non-covalent attachment of a reporter molecule.

A variety of protocols for measuring the presence of mutant $GABA_A$ receptors, including ELISAs, RIAs, and FACS, are known in the art and provide a basis for diagnosing epilepsy and/or anxiety and/or manic depression and/or phobic obsessive symptoms and/or Alzheimer's disease and/or schizophrenia and/or migraine and/or obesity. The expression of a mutant receptor is established by combining body fluids or cell extracts taken from test mammalian subjects, preferably human, with antibody to the receptor under conditions suitable for complex formation. The amount of complex formation may be quantitated by various methods, preferably by photometric means. Antibodies specific for the mutant receptor will only bind to individuals expressing the said mutant receptor and not to individuals expressing only wild-type receptors (ie normal individuals). This establishes the basis for diagnosing the disease.

Once an individual has been diagnosed with the disorder, effective treatments can be initiated. These may include administering a selective modulator of the mutant receptor or an antagonist to the mutant receptor such as an antibody or mutant complement as described above. Alternative treatments include the administering of a selective agonist or modulator to the mutant receptor so as to restore receptor function to a normal level or introduction of wild-type receptor, particularly through gene therapy approaches as described above. Typically, a vector capable of a expressing the appropriate full length $GABA_A$ receptor subunit or a fragment of derivative thereof may be administered.

In an alternative support approach to therapy, a substantially purified $GABA_A$ receptor or $GABA_A$ receptor subunit polypeptide and a pharmaceutically acceptable carrier may be administered as described above.

In further embodiments, oligonucleotides or longer fragments derived from any of the polynucleotide sequences described herein may be used as probes in a microarray. The microarray can be used to monitor the expression level of large numbers of genes simultaneously and to identify genetic variants, mutations, and polymorphisms. This information may be used to determine gene function, to understand the genetic basis of a disorder, to diagnose a disorder, and to develop and monitor the activities of therapeutic agents. Microarrays may be prepared, used, and analyzed using methods known in the art. (For example, see Schena et al., 1996; Heller et al., 1997).

The present invention also provides for the production of genetically modified (knock-out, knock-in and transgenic), non-human animal models transformed with the DNA molecules of the invention. These animals are useful for the study of the function of a GABA receptor, to study the mechanisms of disease as related to a GABA receptor, for the screening of candidate pharmaceutical compounds, for the creation of explanted mammalian cell cultures which express a mutant $GABA_A$ receptor and for the evaluation of potential therapeutic interventions.

Animal species which are suitable for use in the animal models of the present invention include, but are not limited to, rats; mice, hamsters, guinea pigs, rabbits, dogs, cats, goats, sheep, pigs, and non-human primates such as monkeys and chimpanzees. For initial studies, genetically modified mice and rats are highly desirable due to their relative ease of maintenance and shorter life spans. For certain studies, transgenic yeast or invertebrates may be suitable and preferred because they allow for rapid screening and provide for much easier handling. For longer term studies, non-human primates may be desired due to their similarity with humans.

To create an animal model for a mutated GABA receptor several methods can be employed. These include but are not limited to generation of a specific mutation in a homologous animal gene, insertion of a wild type human gene and/or a humanized animal gene by homologous recombination, insertion of a mutant (single or multiple) human gene as genomic or minigene cDNA constructs using wild type or mutant or artificial promoter elements or insertion of artificially modified fragments of the endogenous gene by homologous recombination. The modifications include insertion of mutant stop codons, the deletion of DNA sequences, or the inclusion of recombination elements (lox p sites) recognized by enzymes such as Cre recombinase.

To create a transgenic mouse, which is preferred, a mutant version of a particular $GABA_A$ receptor subunit can be inserted into a mouse germ line using standard techniques of oocyte microinjection or transfection or microinjection into embryonic stem cells. Alternatively, if it is desired to inactivate or replace an endogenous $GABA_A$ receptor subunit gene, homologous recombination using embryonic stem cells may be applied.

For oocyte injection, one or more copies of the mutant $GABA_A$ receptor subunit gene can be inserted into the pronucleus of a just-fertilized mouse oocyte. This oocyte is then reimplanted into a pseudo-pregnant foster mother. The liveborn mice can then be screened for integrants using analysis of tail DNA or DNA from other tissues for the presence of the particular human subunit gene sequence. The transgene can be either a complete genomic sequence injected as a YAC, BAC, PAC or other chromosome DNA fragment, a complete cDNA with either the natural promoter or a heterologous promoter, or a minigene containing all of the coding region and other elements found to be necessary for optimum expression.

According to a further aspect of the present invention, neurological material obtained from animal models generated as a result of the identification of specific $GABA_A$ receptor subunit human mutations, particularly those disclosed in the present invention, can be used in microarray experiments. These experiments can be conducted to identify the level of expression of particular GABA receptor subunits or any cDNA clones from whole-brain libraries in epileptic brain tissue as opposed to normal control brain tissue. Variations in the expression level of genes, including $GABA_A$ receptor subunits, between the two tissues indicates their involvement in the epileptic process either as a cause or consequence of the original $GABA_A$ receptor mutation present in the animal model. Microarrays may be prepared, used, and analyzed using methods known in the art. (For example, see Schena et al., 1996; Heller et al., 1997).

According to still another aspect of the invention there is provided the use of genetically modified non-human animals as described above for the screening of candidate pharmaceutical compounds.

It will be clearly understood that, although a number of prior art publications are referred to herein, this reference does not constitute an admission that any of these documents forms part of the common general knowledge in the art, in Australia or in any other country.

Throughout this specification and the claims, the words "comprise", "comprises" and "comprising" are used in a non-exclusive sense, except where the context requires otherwise.

In one embodiment, an isolated mammalian polypeptide is disclosed, wherein the said polypeptide comprises a mutant γ-aminobutyric acid type A ($GABA_A$) receptor subunit, wherein a mutation event selected from the group consisting of substitutions, deletions, truncations, insertions and rearrangements has occurred and the mutation event disrupts the functioning of an assembled $GABA_A$ receptor, or an otherwise functional fragment or homologue thereof. Optionally, the polypeptide comprises a mutant γ-aminobutyric acid type A ($GABA_A$) receptor subunit, wherein a mutation event creates a phenotype of epilepsy and/or anxiety and/or manic depression and/or phobic obsessive symptoms and/or Alzheimer's disease and/or schizophrenia and/or migraine and/or obesity. Also optionally, the isolated mammalian polypeptide comprise a $GABA_A$ gamma subunit, including but not limited to a gamma-2 subunit.

The mutation event can occur in an extracellular region of the gamma-2 subunit. The mutation event can abolish or reduc diazepam potentiation of the GABA response. The mutation event can occur in a benzodiazepine binding domain. In this case, one mutation event can occur in the large extracellular loop of the gamma-2 subunit.

In certain embodiments mutation event can be a substitution. For example, the mutation event can result in replacement of a highly conserved arginine at residue 43 of the mature gamma-2 subunit, or in replacement of the highly conserved arginine with a glutamine. By way of additional example, an isolated mammalian polypeptide of the present invention can have the amino acid sequence set forth in SEQ ID NO:4. Further, the one or more additional mutation events can be selected from the group consisting of substitutions, deletions, truncations, insertions and rearrangements. The one or more mutation events can be conservative substitutions. An isolated mammalian polypeptide can comprise the amino acid sequence set forth in SEQ ID NQ:4. An isolated mammalian polypeptide as disclosed herein can consist of the amino acid sequence set forth in SEQ ID NO:4.

In another embodiment of an isolated mammalian polypeptide of the present invention, the mutation event occurs in a large cytoplasmic loop between the third and fourth membrane spanning domain of the gamma-2 subunit protein. In this case, the mutation event can be a truncation, such as but not limited to a deletion is from position 351 of the mature gamma-2 subunit. By way of additional example, an isolated mammalian polypeptide of the present invention can have the amino acid sequence set forth in SEQ ID NO:5. Further, an isolated mammalian polypeptide of the present invention can comprise one or more additional mutation events selected from the group consisting of substitutions, deletions, truncations, insertions and rearrangements. The one or more mutation events can be conservative substitutions. An isolated mammalian polypeptide can comprise the amino acid sequence set forth in SEQ ID NO:5. An isolated mammalian polypeptide can consist of the amino acid sequence set forth in SEQ ID NO:5.

In another embodiment of an isolated mammalian polypeptide of the present invention, the mutant subunit is a $GABA_A$ delta subunit. The mutation event can occur in an extracellular region of the $GABA_A$ delta subunit. The mutation event can occur in the large extracellular loop of the $GABA_A$ delta subunit. The mutation event can be a substitution, such as but not limited to a replacement of an arginine at residue 172 of the mature delta subunit. For example, the mutation event can result in replacement of an arginine with a cysteine. By way of additional example, an isolated mammalian polypeptide of the present invention can have the amino acid sequence set forth in SEQ ID NO:6. Further, one or more additional mutation events selected from the group consisting of substitutions, deletions, truncations, insertions and rearrangements can occur. The one or more mutation events can be conservative substitutions.

An isolated mammalian polypeptide as disclosed herein can comprise the amino acid sequence in SEQ ID NO:6. An isolated mammalian polypeptide as disclosed herein can comprise the amino acid sequence set forth in SEQ ID NO:6.

In the foregoing embodiments, an isolated mammalian polypeptidecan be an assembled $GABA_A$ receptor including a subunit as disclosed herein.

Also disclosed herein is an antibody which is immunologically reactive with a polypeptide according to the present invention, but not with a wild-type $GABA_A$ receptor or subunit thereof.

A method of treating epilepsy and/or anxiety and/or manic depression and/or phobic obsessive symptoms and/or Alzheimer's disease and/or schizophrenia and/or migraine and/or obesity, is also disclosed. In one embodiment, the method comprises the step of administering a wild-type $GABA_A$ receptor or receptor subunit and/or an isolated DNA molecule encoding a wild-type $GABA_A$ receptor or receptor subunit or an agonist or modulator of the $GABA_A$ receptor to replace $GABA_A$ receptor activity, or an agonist or modulator of a mutant $GABA_A$ receptor as defined herein to restore $GABA_A$ receptor activity, in a patient in need of such treatment. Optionally, diazepam potentiation is restored, and receptor function can optionally be restored through the incorporation of truncated $GABA_A$ receptors into the cell membrane.

Also optionally, activity of the subject's functional receptors can be increased. In this embodiment, a wild-type $GABA_A$ receptor or a $GABA_A$ receptor subunit is introduced by gene therapy.

By way of additional example, a wild-type $GABA_A$ gamma or delta subunit can be introduced.

The use of a wild-type $GABA_A$ receptor or receptor subunit and/or an isolated DNA molecule encoding a wild-type $GABA_A$ receptor or receptor subunit or an agonist or modulator of a wild-type or mutant $GABA_A$ receptor in the manufacture of a medicament for the treatment of epilepsy and/or anxiety and/or manic depression and/or phobic obsessive symptoms and/or Alzheimer's disease and/or schizophrenia and/or migraine and/or obesity is also disclosed.

Also disclosed is a method of treating epilepsy and/or anxiety and/or manic depression and/or phobic obsessive symptoms and/or Alzheimer's disease and/or schizophrenia and/or migraine and/or obesity, comprising administering a selective antagonist or modulator of a mutant $GABA_A$ receptor as defined herein. Optionally, the selective antagonist or modulator is an antibody. Optionally, the antibody is selected from the group comprising of polyclonal antibodies, monoclonal antibodies, chimeric, single chain antibodies and antibody fragments such as F(ab')2 and Fab.

Also disclosed is the use of a selective antagonist or modulator of a mutant $GABA_A$ receptor as disclosed in the present invention in the manufacture of a medicament for the treatment of epilepsy and/or anxiety and/or manic depression and/or phobic obsessive symptoms and/or Alzheimer's disease and/or schizophrenia and/or migraine and/or obesity.

A method of treating epilepsy and/or anxiety and/or manic depression and/or phobic obsessive symptoms and/or Alzheimer's disease and/or schizophrenia and/or migraine and/or obesity, is disclosed. In one embodiment, the method comprises administering a DNA molecule which is the complement of any one of the isolated mammalian DNA molecules defined in the present invention to a subject in need of such treatment.

Also disclosed is the use of a DNA molecule which is a complement of an isolated mammalian DNA molecule as disclosed in the present invention in the manufacture of a medicament for the treatment of epilepsy and/or anxiety and/or manic depression and/or phobic obsessive symptoms and/or Alzheimer's disease and/or schizophrenia and/or migraine and/or obesity.

Also disclosed is the use of an isolated mammalian DNA molecule of the present invention for the diagnosis of epilepsy and/or anxiety and/or manic depression and/or phobic obsessive symptoms and/or Alzheimer's disease and/or schizophrenia and/or migraine and/or obesity.

Also disclosed is the use of a polypeptide of the present invention in the diagnosis of epilepsy and/or anxiety and/or manic depression and/or phobic obsessive symptoms and/or Alzheimer's disease and/or schizophrenia and/or migraine and/or obesity.

Also disclosed is the use of an antibody of the present invention in the diagnosis of epilepsy and/or anxiety and/or manic depression and/or phobic obsessive symptoms and/or Alzheimer's disease and/or schizophrenia and/or migraine and/or obesity.

A method for the diagnosis of epilepsy and/or anxiety and/or manic depression and/or phobic obsessive symptoms and/or Alzheimer's disease and/or schizophrenia and/or migraine and/or obesity is also disclosed. In one embodiment, the method comprises the steps of obtaining DNA from a subject suspected of epilepsy and/or anxiety and/or manic depression and/or phobic obsessive symptoms and/or migraine and/or obesity and/or Alzheimer's disease; and comparing the DNA sequence of a subunit of the $GABA_A$ receptor of said DNA to the DNA sequence of the corresponding subunit of the wild-type $GABA_A$ receptor.

In this embodiment each DNA fragment can be sequenced and the sequences compared. Further, the DNA fragments can be subjected to restriction enzyme analysis and/or subjected to SSCP analysis.

A method for the diagnosis of epilepsy and/or anxiety and/or manic depression and/or phobic obsessive symptoms and/or Alzheimer's disease and/or schizophrenia and/or migraine and/or obesity is also disclosed. In one embodiment, the method comprises the steps of obtaining a $GABA_A$ receptor from a subject suspected of epilepsy and/or anxiety and/or manic depression and/or phobic obsessive symptoms and/or Alzheimer's disease and/or schizophrenia and/or migraine and/or obesity; and comparing a subunit of said receptor with the corresponding subunit of the wild-type $GABA_A$ receptor.

BRIEF DESCRIPTION OF THE DRAWINGS

Preferred forms of the invention are described, by way of example only, with reference to the following examples and the accompanying drawings, in which:

FIG. 3 indicates the position of the c245G→A mutation present in the $GABA_A$ receptor gamma-2 subunit (GABRG2) gene in Family 1. a: The sequencing trace shows a portion of exon 2 of GABRG2. The upper panel represents the mutated sequence, while the lower panel represents the wild-type sequence. The top arrow indicates the position of the nucleotide base change. The position of the mutation in the GABRG2 protein is indicated by the bottom arrow. b: Alignment of $GABA_A$ receptor subunit proteins with other ligand-gated receptor subunits. The conserved arginine (R) residue is boxed.

MODES FOR PERFORMING THE INVENTION

EXAMPLE 1

Clinical Diagnosis of Affected Family Members

Figure 1:
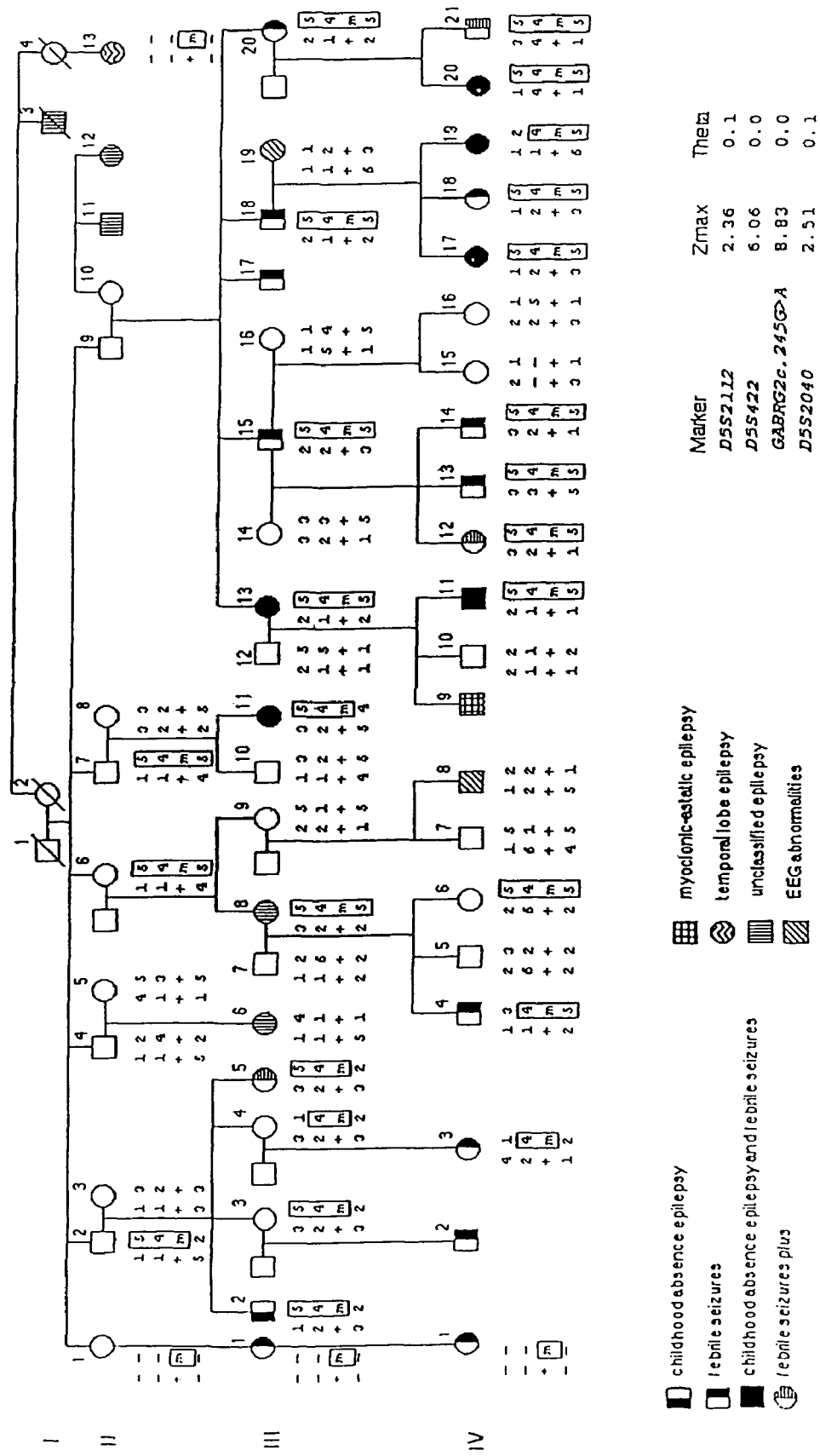
FIG. 1 is the pedigree of Family 1, a four-generation family with childhood absence epilepsy and febrile seizures. Unaffected branches that were not genotyped are omitted. The disease-associated haplotype is boxed. The presence of the R43Q mutation is indicated by an 'm'. The two-point lod scores associated with the disease haplotype are also indicated.

Individuals from three families were used in this study with informed consent being obtained from all participating subjects. The first family whose pedigree is shown in FIG. 1 originated in the United Kingdom and information was obtained on 192 individuals over 4 generations, with most living members residing in the Australian state of Victoria. Of the 29 individuals with a history of seizures, 7 had childhood absence epilepsy (CAE), including 6 with prior febrile seizures (FS). An additional 12 individuals had typical FS and a further 3 had the extended phenotype of febrile seizures plus (FS$^+$). The remaining 7 affected individuals included 1 with a more severe generalised epilepsy phenotype (myoclonic-astatic epilepsy), 1 with temporal lobe epilepsy, and 5 with unclassified epilepsy. An additional 2 individuals without seizures had generalised spike-wave discharges on electroencephalogram (EEG). The mean age of onset of FS was 13 months and of CAE was 3 years. The pedigree suggests possible generation-dependent penetrance. This is probably due to two factors: bilineal inheritance and the lack of reliable early childhood histories in older individuals.

Figure 2:
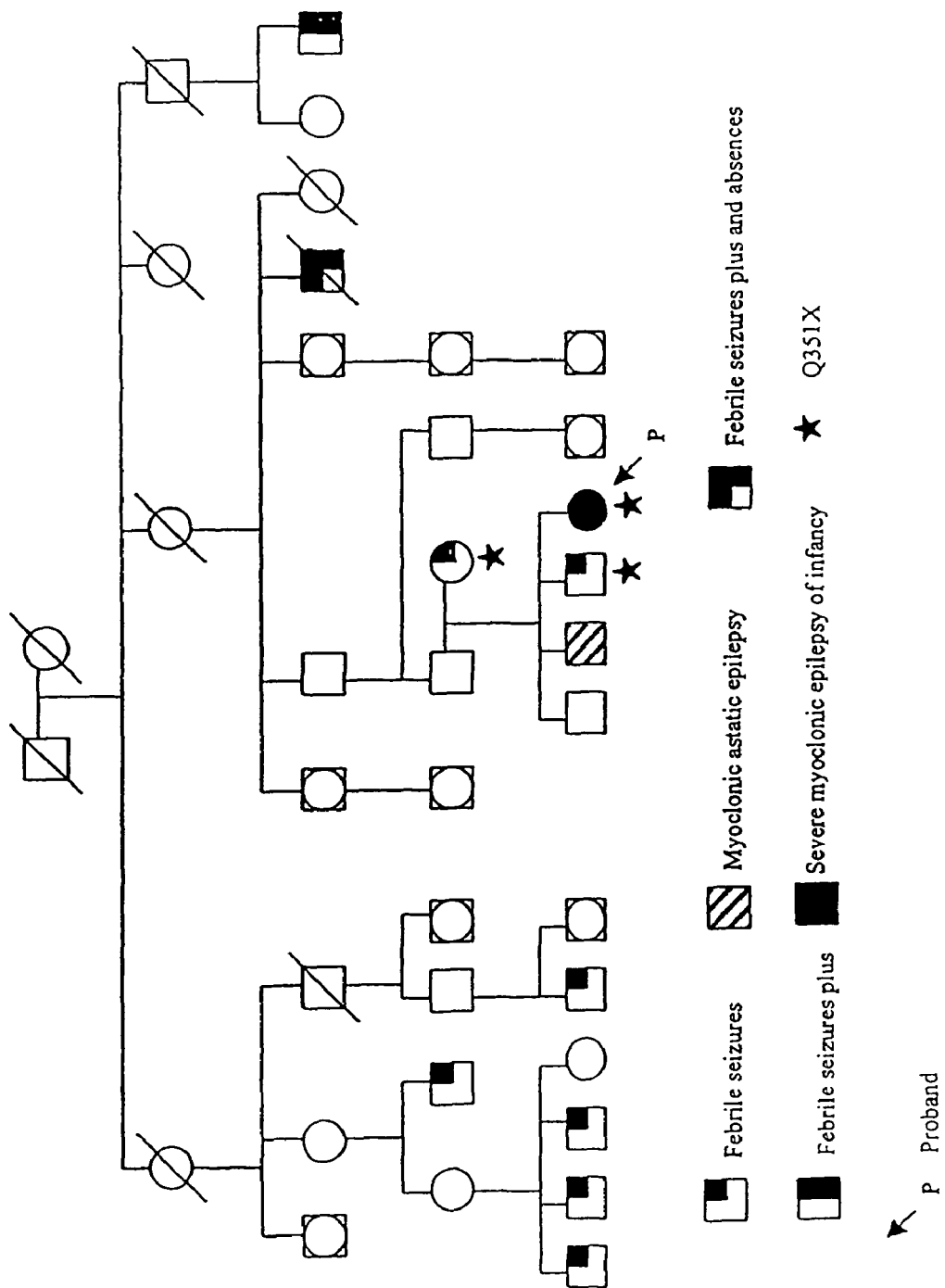
FIG. 2 is the pedigree of Family 2, in which idiopathic generalised epilepsy is also present. The figure demonstrates the clinical heterogeneity that exists within the family. The proband in which the Q351X mutation was identified had severe myoclonic epilepsy of infancy. The Q351X mutation was also identified in the probands brother and mother, both of which were classified with febrile seizures.

The second family whose pedigree is shown in FIG. 2 had generalised epilepsy with febrile seizures plus (GEFS$^+$ or FS$^+$) and was ascertained through the proband who suffered severe myoclonic epilepsy of infancy (SMEI). There was a bilineal family history of epilepsy, with 8 affected individuals on the father's side and 3 on the mother's. The mother, her brother and his daughter were thought to have had FS. The proband with SMEI had onset at age 3 months with focal FS, followed by the evolution of multiple seizure types with prominent myoclonus and mild intellectual disability. Her EEG showed generalised polyspike-wave with photosensitivity. Two of her three brothers were affected, one with FS and one with myoclonic-astatic epilepsy (MAE). The boy with MAE had onset at 2 months with myoclonic and absence seizures. Generalised tonic-clonic seizures started at 4 years. His EEG showed generalised polyspike-wave with photosensitivity. He also had mild intellectual disability. On the father's side, there were 6 individuals with FS and 2 with FS and epilepsy. Not all of the individuals from Family 2 clinically described above are shown in the pedigree of this family represented by FIG. 2.

The third family had generalised epilepsy with febrile seizures plus (GEFS$^+$ or FS$^+$) with many individuals from the family not yet clinically characterised. The proband and his identical twin brother have GEFS$^+$.

Blood was obtained for DNA extraction from 47 members of Family 1, including 23 individuals with seizures, from 14 members of Family 2, including 6 affected individuals and from the identical twin boys and their mother in Family 3. Methods for DNA extraction included the use of the QIAamp DNA Blood Maxi kit (Qiagen) according to manufacturers specifications or through procedures adapted from Wyman and White (1980).

EXAMPLE 2

Genotyping and Linkage Analysis

Automated genotyping of DNA samples obtained from Family 1 was carried out by the Australian Genome Research Facility. A genome-wide scan of 400 markers spread at an average genetic distance of 10 cM was performed. For the linkage analysis, all individuals with febrile seizures (FS), febrile seizures plus (FS$^+$) or childhood absence epilepsy (CAE) were considered affected. Those individuals with unclassified epilepsy or abnormal electroencephalograms were assigned an unknown affection status. Lod scores were determined using FASTLINK v4.0P (Lathrop and Lalouel, 1984). Two point lod scores were calculated assuming autosomal dominant inheritance, 75% penetrance, a disease allele frequency of 0.0001 and equal marker allele frequencies.

Additional microsatellite markers from chromosome 5 were manually genotyped as previously described by Phillips et al (1995). Briefly, PCR amplification was carried out on 100 ng of genomic DNA using [α-$^{32}$P]dCTP. PCR conditions were 10 cycles of 94° C. for 1 minute, 60° C. for 1.5 minutes and 72° C. for 1.5 minutes, followed by 25 cycles at 94° C. for 1 minute, 55° C. for 1.5 minutes and 72° C. for 1.5 minutes. A final extension step of 10 minutes at 94° C. concluded the PCR reaction. Products were separated on 5% denaturing polyacrylamide gels and visualized by autoradiography after exposure for 1–3 days at −70° C.

Results from the genome screen revealed a linked marker on chromosome 5 (D5S422) that segregated with individuals previously classified as affected (CAE, FS or FS$^+$) with a lod score of 6.06 at θ=0.0). Recombination between the disease allele and markers D5S2112 and D5S2040 placed the affected gene within a 9.3 cM region on chromosome 5q32–q33 (FIG. 1). Neither of the family members with EEG abnormalities only (IV-8 and the marry-in III-19) have the disease-associated allele. DNA was available from three individuals with seizures who were not known to have CAE or FS (II-13, III-6, III-8). Individual III-8 has unclassified epilepsy, but her son has FS and she does carry the disease-associated allele of D5S422. Individual II-13 has temporal lobe epilepsy as an adult and does carry the allele, but it was unknown if she had FS in childhood, as her parents are deceased. Similarly, the lack of reported febrile seizures in the four unaffected individuals with the mutant allele in generation II (II-1, II-2, II-6, II-7) and the untested obligate carrier (II-9) may be due to the lack of reliable childhood histories in these elderly individuals. Individual III-6, who had an unclassified seizure disorder (and was not defined as affected), was the only individual, of those tested with seizures, without the mutated allele. Given the high prevalence of epilepsy in the population, she is likely to be a phenocopy.

A search of the Human Gene Map '99 (www.ncbi.nlm.nih.gov/genemap/) revealed a cluster of four $GABA_A$ receptor subunits, alpha-1 (GABRA1), alpha-6 (GABRA6), beta-2 (GABRB2) and gamma-2 (GABRG2), that were positioned close to D5S422 and hence were considered candidate genes for epilepsy associated mutations. In silico database analysis of the GABRG2 nucleotide sequence enabled the determination of the genomic structure of the gene (Table 1) facilitating the design of primers in the intronic sequence spanning each exon. This subsequently enabled the amplification of each of the 9 exons of the GABRG2 gene from genomic DNA of family members allowing each exon to be screened for mutations by single stranded conformation polymorphism (SSCP) analysis.

EXAMPLE 3

Mutation Analysis of GABRG2 in Family 1

SSCP analysis of GABRG2 exons followed by sequencing of SSCP bandshifts was performed on individuals from Family 1 to identify disease causing mutations. The primers used to analyse Family 1 are shown in Table 2. The sequences of these primers are represented by SEQ ID Numbers:7–24.

PCR reactions using exon specific primers contained 67 mM Tris-HCl (pH 8.8); 16.5 mM $(NH_4)_2SO_4$; 6.5 µM EDTA; 1.5 mM $MgCl_2$; 200 µM each dNTP; 10% DMSO; 0.17 mg/ml BSA; 10 mM β-mercaptoethanol; 15 µg/ml each primer; 200 µCi/ml [α-32P]dCTP; 100 U/ml Taq DNA polymerase, and 10 µg/ml genomic DNA. PCR reactions were performed using 10 cycles of 94° C. for 60 seconds, 60° C. for 90 seconds, and 72° C. for 90 seconds followed by 25 cycles of 94° C. for 60 seconds, 55° C. for 90 seconds, and 72° C. for 90 seconds. A final extension reaction for 10 minutes at 72° C. followed. Completed PCR reactions were subsequently mixed with an equal volume of formamide loading buffer (96% formamide; 1 mM EDTA; 0.1% bromophenol blue; 0.1% xylene cyanol) and were heated to 95° C. for 5 minutes before snap cooling on ice. Three µl of each sample was then loaded onto 37.5% MDE™ gels containing 5% glycerol and 0.6×TBE. The gels were run at 700 volts for 20 hours at room temperature and exposed to X-ray film at −70° C.

PCR products showing a conformational change were subsequently sequenced. This first involved re-amplification of the amplicon from the relevant individual followed by purification of the PCR amplified templates for sequencing using QiaQuick PCR preps (Qiagen) based on manufacturers procedures. The primers used to sequence the purified GABRG2 amplicons were identical to those used for the initial amplification step. For each sequencing reaction, 25 ng of primer and 100 ng of purified PCR template were used. The BigDye sequencing kit (ABI) was used for all sequencing reactions according to the manufacturers specifications. The products were run on an ABI 377 Sequencer and analysed using the EditView program.

SSCP analysis and sequencing of exon 2 in this family revealed a G to A nucleotide substitution at position 471 (c245G→A) of the GABRG2 gene (FIG. 3a). The c245G→A mutation changes a highly conserved arginine amino acid to glutamine at residue 43 (R43Q) of the mature GABRG2 protein or residue 82 (R82Q) of the precursor protein. The amino acid residue numbering will be based on the mature protein in subsequent descriptions. The R43Q change was detected in all family members carrying the disease associated allele but was not detected in 140 control chromosomes from the normal population. In addition, sequence conservation at this site is seen in many other human and animal $GABA_A$ receptor subunits as well as other ligand-gated receptor subunits (FIG. 3b). This provides circumstantial evidence for the functional importance of this residue.

EXAMPLE 4

Mutation Analysis of GABRG2 in Family 2

SSCP analysis of GABRG2 exons followed by sequencing of SSCP bandshifts was performed on individuals from Family 2 to identify disease causing mutations. The primers used to analyse Family 2 are shown in Table 3. The sequences of these primers are represented by SEQ ID Numbers:7–17, 19–24 and 25–29.

For the analysis of this family primers used for SSCP were labelled at their 5' end with HEX. Typical PCR: reactions were performed in a total volume of 10 µl using 30 ng of patient DNA. All PCR reactions contained 67 mM Tris-HCl (pH 8.8); 16.5 mM $(NH_4)_2SO_4$; 6.5 µM EDTA; 1.5 mM $MgCl_2$; 200 µM each dNTP; 10% DMSO; 0.17 mg/ml BSA; 10 mM β-mercaptoethanol; 5 µg/ml each primer and 100 U/ml Taq DNA polymerase. PCR reactions were performed using 10 cycles of 94° C. for 30 seconds, 60° C. for 30 seconds, and 72° C. for 30 seconds followed by 25 cycles of 94° C. for 30 seconds, 55° C. for 30 seconds, and 72° C. for 30 seconds. A final extension reaction for 10 minutes at 72° C. followed.

Twenty µl of loading dye comprising 50% (v/v) formamide, 12.5 mM EDTA and 0.02% (w/v) bromophenol blue were added to completed reactions which were subsequently run on non-denaturing 4% polyacrylamide gels with a cross-linking ratio of 35:1 (acrylamide:bis-acrylamide) and containing 2% glycerol. Gel thickness was 100 µm, width 168 mm and length 160 mm. Gels were run at 1200 volts and approximately 20 mA, at 22° C. and analysed on the GelScan 2000 system (Corbett Research, Australia) according to manufacturers specifications.

PCR products showing a conformational change were subsequently sequenced as described for Family 1. However, the primers used for the re-amplification of a specific exon in which an SSCP change was seen, did not contain the 5' HEX label. The re-amplified exons were purified using QiaQuick PCR preps (Qiagen) based on manufacturers procedures. The primers used to sequence the purified GABRG2 amplicons were identical to those used for the initial re-amplification step. For each sequencing reaction, 25 ng of primer and 100 ng of purified PCR template were used. The BigDye sequencing kit (ABI) was used for all sequencing reactions according to the manufacturers specifications. The products were run on an ABI 377 Sequencer and analysed using the EditView program.

Figure 4:
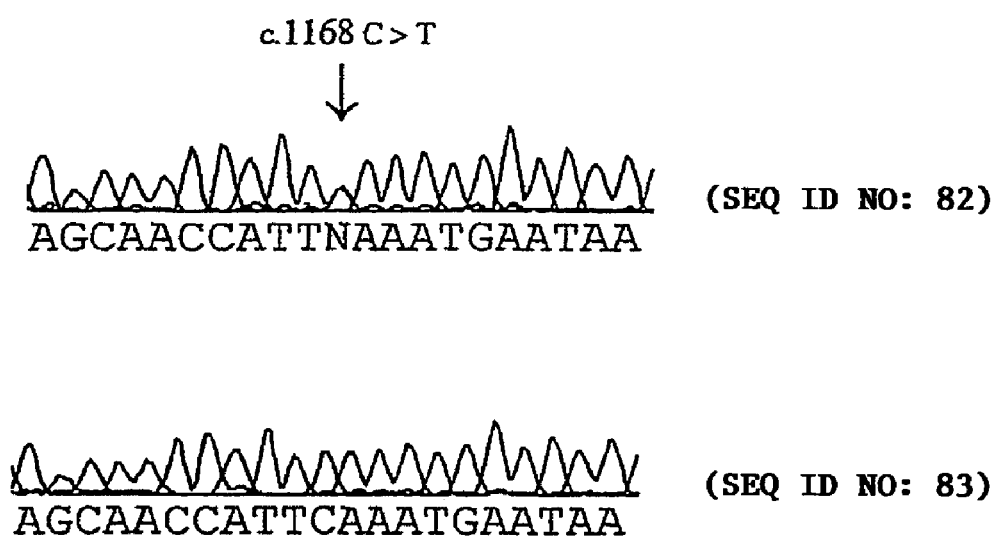
FIG. 4 shows the position of the mutation in the $GABA_A$ receptor gamma-2 subunit (GABRG2) gene in Family 2. The sequencing trace shows a portion of exon 9 of the gene with the upper panel indicating the C→T change that results in a CAA (glutamine) to TAA (stop codon) codon change. The lower sequencing trace represents that of the wild-type GABRG2 gene.

SSCP analysis of exon 9 in this family identified a bandshift in the proband. Upon sequencing of this variant, a C to T nucleotide change was observed at position 1394 (c1168C→T) within exon 9 of the GABRG2 gene (FIG. 4). The same nucleotide substitution was also observed in her brother and mother. The c1168C→T mutation changes a highly conserved glutamine amino acid to a stop codon at residue 351 (Q351X) of the mature GABRG2 protein, giving rise to a truncated protein missing the fourth membrane spanning domain. The Q351X mutation was not observed in any other samples tested during the SSCP screen. Loss of the fourth transmembrane domain of the GABRG2 protein is suspected to cause major problems with the functioning and/or assembly of the receptor complex.

EXAMPLE 5

Mutation Analysis of GABRD in Family 3

Due to the involvement of the GABRG2 gene in epilepsy as disclosed in this invention, mutation analysis of other $GABA_A$ receptor subunits was initiated. SSCP analysis of GABRD exons followed by sequencing of SSCP bandshifts was performed on individuals from Family 3 to identify disease causing mutations. The primers used to analyse Family 3 are shown in Table 4. The sequences of these primers are represented by SEQ ID Numbers:30–49. SSCP analysis of exon 1 was not completed due to the lack of genomic sequence being available spanning this exon.

As with the analysis of Family 2 above, primers for the analysis of the GABRD gene in Family 3 were labeled at their 5' end with HEX. PCR conditions were identical to those described above for the analysis of Family 2. Exons in which an SSCP change was observed were sequenced, as described above, to identify the basis for this change.

SSCP analysis of GABRD in this family identified a bandshift in the proband. Upon sequencing of this variant, a C to T nucleotide change was observed at position c658 within the GABRD gene. This nucleotide change results in an arginine amino acid being replaced with a cysteine residue. This mutation was also observed in the probands identical twin brother and their mother but was not observed in 192 control chromosomes from the normal population.

EXAMPLE 6

Functional Significance of the GABRG2 Mutations

To test the effects of the GABRG2 mutations on $GABA_A$ receptor function, electrophysiological analysis of *Xenopus laevis* oocytes were conducted. cDNAs encoding the GABRA1, GABRB2 and GABRG2 subunits of the human $GABA_A$ receptor were subcloned into pcDNA3.1(+). The c245G→A and c1168C→T mutations were introduced separately into GABRG2 of the human $GABA_A$ receptor using the QuickChange site directed mutagenesis kit (Stratagene, La Jolla, Calif.). The oligonucleotide represented by SEQ ID NO:50 (5' GGA TAT GAC AAT AAA CTT CAG CCT GAT ATA GGA GTG AAG CC 3') was used to incorporate the c245G→A mutation, while the oligonucleotide represented by SEQ ID NO:51 (5' GCG AAT TCA TTA AAT GGT TGC TGA TCT TGG GCG 3') was used to incorporate the c1168C→T mutation. Successful mutagenesis was identified by DNA sequencing. Wild-type and mutant cDNAs were linearised and gel purified and cRNA was made using the T7 RNA polymerase Message Machine in vitro RNA synthesis kit (Ambion). Samples of cRNA were run on denaturing agarose gels to ensure they were the correct size and were not degraded. *Xenopus laevis* oocytes (stage V or VI) were microinjected with ~25 ng of cRNA representing the $GABA_A$ subunits. A tenfold molar excess of wild-type and mutant GABRG2 was used to promote assembly of the ternary (GABRA1:GABRB2:GABRG2) rather than binary (GABRA1:GABRB2) complex. Oocytes were then stored in OR2 buffer (82.5 mM NaCl, 2 mM KCl, 1 mM $MgCl_2$, 5 mM HEPES, pH 7.5, supplemented with 2% foetal bovine serum, 100 U/ml penicillin, 100 µg/ml streptomycin, Life Technologies) and incubated at 18° C. for three to five days to allow for adequate receptor expression. Current recordings from oocytes were made using a two-electrode voltage clamp (AxoClamp 2B, Axon Instruments), with recordings made at a holding potential of −80 mV. Electrodes were filled with 3 M KCl and were of 1–2 MΩ resistance. Oocytes were continuously perfused with ND96 solution (96 mM NaCl, 2 mM KCl, 1 mM $MgCl_2$, 1.8 mM $BaCl_2$ and 5 mM HEPES, pH 7.5). gamma-Aminobutyric acid (GABA; Sigma-Aldrich, Australia) was applied by bath perfusion.

c245G→A (R43Q) Mutation

Figure 5:
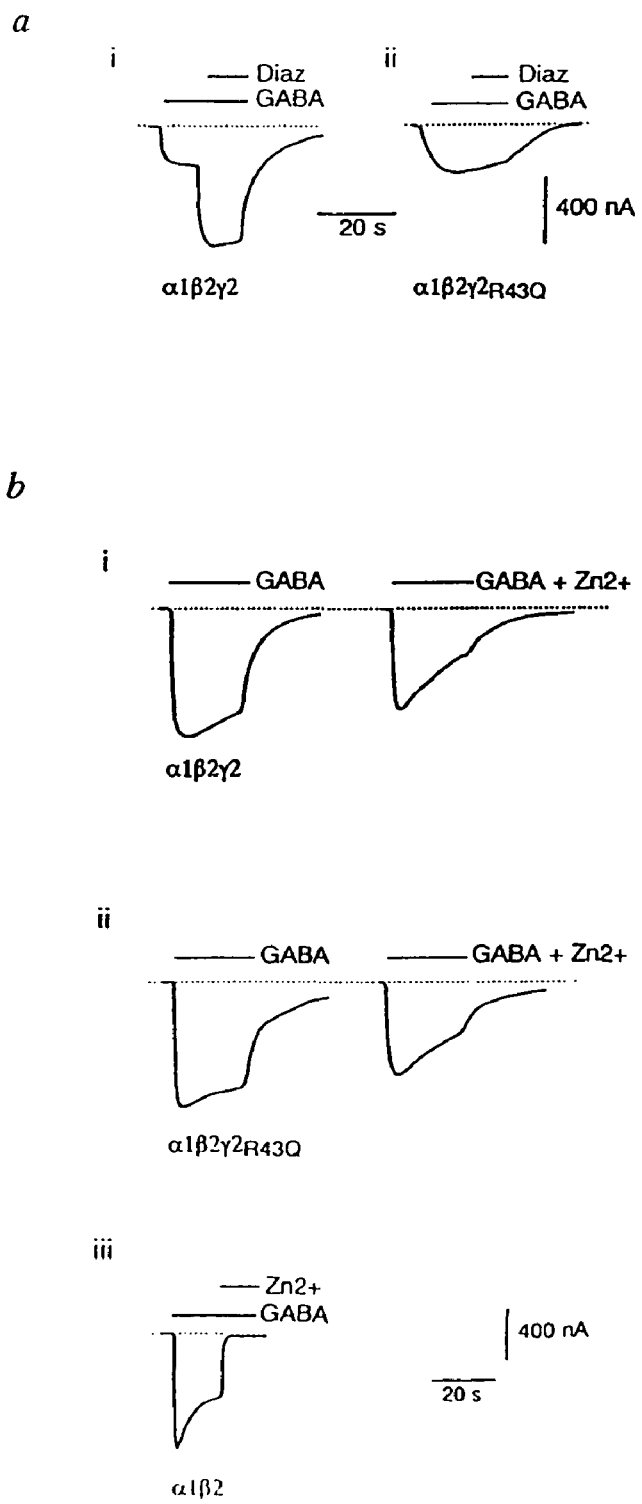
FIG. 5 illustrates electrophysiological analyses of GABRG2 and the GABRG2(R43Q) mutant in *Xenopus laevis* oocytes. a: The R43Q mutation of GABRG2 abolishes diazepam potentiation of GABA currents. Wild-type GABRA1:GABRB2:GABRG2 (α1β2γ2) (i) and mutant GABRA1:GABRB2:GABRG2(R43Q) [α1β2γ2 (R43Q)] channel responses (ii) to GABA (1 μM) and diazepam (Diaz; 1 μM). Diazepam significantly (P<0.01) increased currents in wild type (302±33%; mean±SEM; n=20) when compared to mutant channels where a small, insignificant, decrease was seen (10%±6% ; mean±SEM; n=17). b: Functional expression of GABRG2(R43Q) revealed by reduced $Zn^{2+}$ sensitivity. Comparison of $Zn^{2+}$ (10 μM) sensitivity of GABA-activated currents from wild-type (α1β2γ2) channels (i) and mutant [α1β2γ2 (R43Q)] channels (ii). In both cases, only partial inhibition (wild-type, 37±2%; mutant, 40±5%) of the GABA current was observed in the presence of $Zn^{2+}$, indicating functional expression of GABRG2 (n=9 for each). Co-expression GABRA1 and GABRB2 (α1β2) alone (iii) revealed a GABA (100 μM)-activated current that was almost completely (89±7%, n=8) abolished by $Zn^{2+}$ (10 μM).

As shown in FIG. 5, the electophysiological responses of the Xenopus oocytes to GABA were found to be indistinguishable in oocytes expressing GABRG2 or GABRG2 (R43Q). However, as arginine 43 is located within the first of two high-affinity benzodiazepine-binding domains (Kucken et al. 2000), it was expected that the mutation may alter diazepam potentiation of GABRG2(R43Q) currents. Additional experiments indicated that while diazepam significantly potentiated currents (303±33%; mean±s.e.m; n=20) in wild-type channels (P<0.01), diazepam potentiation was completely abolished in oocytes expressing receptors containing the GABRG2(R43Q) subunit, in which a small decrease in current was seen (10±6%; mean±s.e.m; n=17; FIG. 5*aii*). As an intermediate diazepam potentiation (129±30%, n=8) was seen in oocytes injected with a 50:50 mixture of GABRG2 and GABRG2(R43Q) cRNA, these observations suggest that R43Q abolishes the actions of benzodiazapines on the GABA receptor.

An alternative explanation could be that the GABRG2 (R43Q) mutation may instead cause incorrect assembly of the GABRG2 subunit with the GABA receptor. The expression of GABRG2 has been shown to be an absolute requirement for benzodiazapine sensitivity (Sigel and Buhr, 1997) with expression of GABRA1 and GABRB2 alone producing GABA-activating currents that are not potentiated by benzodiazapines. As this lack of benzodiazepine sensitivity is qualitatively similar to the results obtained with the GABRG2(R43Q) mutation during this study, we relied on the observation that currents produced by expression of GABRA1 and GABRB2 alone are extremely sensitive to $Zn^{2+}$ while currents produced by the correct assembly of GABRA1, GABRB2 and GABRG2 subunits are significantly less sensitive (Draguhn et al, 1990), to discriminate between the two possibilities. Further experiments indicated that $Zn^{2+}$ had the same effect on GABRG2 and GABRG2 (R43Q) expressing oocytes, indicative of expression and assembly of the mutant subunit (FIG. 5*bi* and *ii*). If the GABRG2(R43Q) subunit did not co-assemble then $Zn^{2+}$ sensitivity would have resembled that seen with GABRA1 and GABRB2 alone. Clearly this was not the case because in oocytes expressing only GABRA1 and GABRB2, GABA-activated currents were totally abolished by $Zn^{2+}$ (FIG. 5biii). Therefore the mutant subunit is expressed and assembles with GABRA1 and GABRB2 and, furthermore, the mutation does not effect $Zn^{2+}$ sensitivity. Thus, the functional consequence of the R43Q mutation of GABRG2 is to abolish diazepam potentiation of the GABA response.

Figure 6:
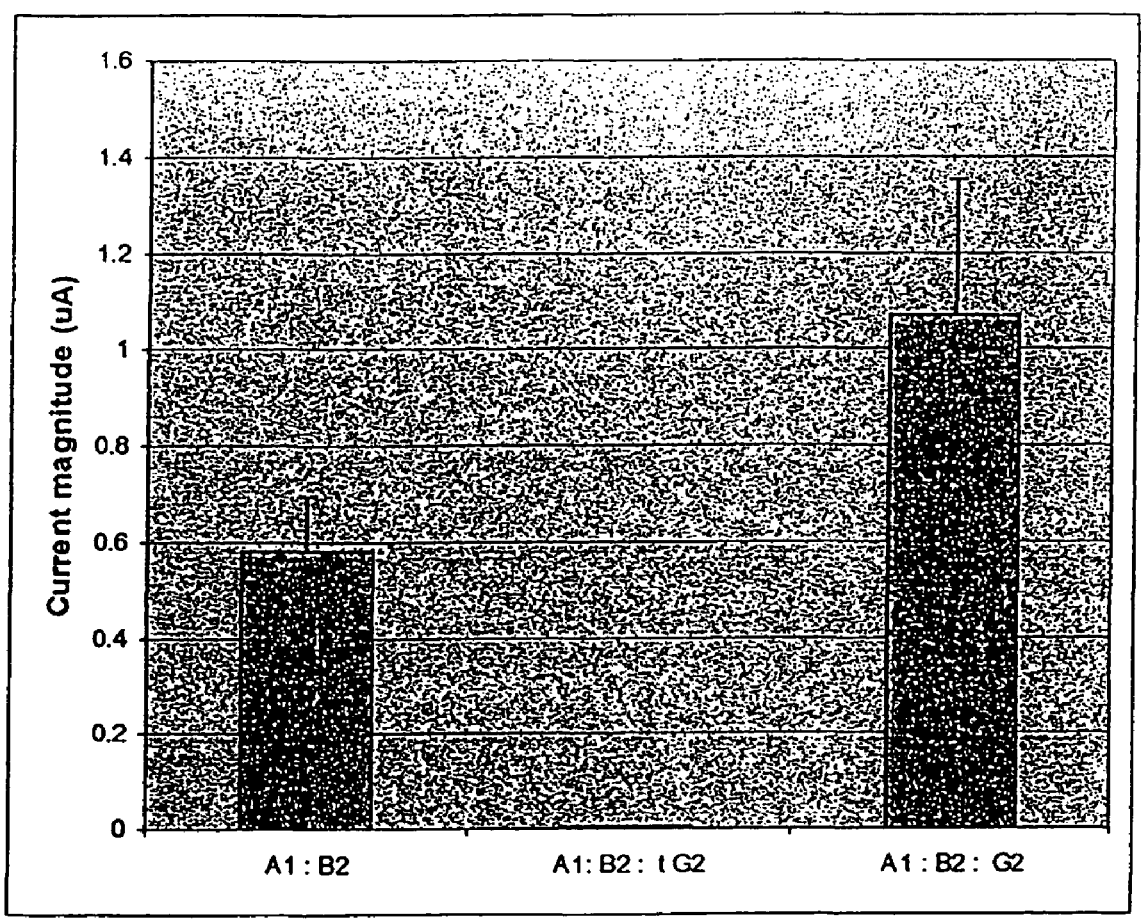
FIG. 6 summarises the results of the electrophysiological analyses of the wild-type $GABA_A$ receptor gamma-2 subunit (GABRG2) and the GABRG2(Q351X) mutant in *Xenopus laevis* oocytes. Expression of the mutant GABRG2 receptor abolishes responses to GABA suggesting it has a dominant negative effect. A comparison of GABA response (measured as current magnitude in μA) in oocytes expressing mutant (Q351X) and wild-type GABRG2 receptors as well as controls expressing GABRA1 and GABRB2 is shown. If truncated receptor did not function, current magnitude would be as for A1/B2 containing receptors. However receptors incorporating truncated GABRG2 abolishes all current suggesting it has a dominant negative effect.

While not wishing to be bound by theory, the loss of benzodiazepine sensitivity caused by the R43Q mutation indicates that the putative natural benzodiazepine receptor ligands (endozepines) may have a physiological role in preventing both febrile seizures and absences. Alternatively, the R43Q mutation in GABRG2 may alter $GABA_A$ receptor function in additional ways in vivo. How this mutation causes the age-dependent expression and temperature-sensitivity of febrile seizures, and the age-dependent expression of CAE is unexplained, but may relate to differential developmental expression and temperature-dependent kinetics of $GABA_A$ or other receptors in the relevant neuronal networks (Brooks-Kayal & Pritchett, 1993).

c1168C→T (Q351X) Mutation:

Using a 1:1:10 (GABRA1:GABRB2:GABRG2(Q351X)) cRNA injection ratio, no current response was observed to GABA. However, controls incorporating wild-type GABRG2 in the above ratios gave strong current responses. In addition, expression of 1:1:10 (GABRA1:GABRB2:water) injection ratios gave current responses to GABA. As the truncated receptor complex did not evoke current magnitude as for GABRA1 and GABRB2 receptor complexes, expression of the mutant GABRG2 receptor has a dominant negative effect (FIG. 6).

The results of these experiments indicate that the GABRG2(Q351X) subunit assembles with the GABRA1 and GABRB2 subunits to produce a non-functional receptor complex. Two possible mechanisms for the inactivity of the receptor are that although it may assemble correctly, the non-functional receptor is secreted to the cell membrane but cannot respond to GABA, or, is unable to be successfully exported to the cell membrane surface and is therefore retained in the lumen of the endoplasmic reticulum (ER). Previous studies of truncated receptors have supported this latter explanation as the lack of a transmembrane anchor (as with the disclosed mutant of the present invention) traps the complex in the ER.

Therefore the $GABA_A$ receptor complex containing GABRG2(Q351X) subunits has a dominant negative effect on the assembled mutant receptor complexes most likely due to a reduction in the density of functional $GABA_A$ receptors leading to decreased inhibitory responses to GABA and thereby increasing neuronal excitability and seizures.

EXAMPLE 7

Analysis of the $GABA_A$ Receptor and Receptor Subunits

The following methods are used to determine the structure and function of the $GABA_A$ receptor and receptor subunits.

Molecular Biological Studies

The ability of the $GABA_A$ receptor as a whole or through individual subunits to bind known and unknown proteins can be examined. Procedures such as the yeast two-hybrid system are used to discover and identify any functional partners. The principle behind the yeast two-hybrid procedure is that many eukaryotic transcriptional activators, including those in yeast, consist of two discrete modular domains. The first is a DNA-binding domain that binds to a specific promoter sequence and the second is an activation domain that directs the RNA polymerase II complex to transcribe the gene downstream of the DNA binding site. Both domains are required for transcriptional activation as neither domain can activate transcription on its own. In the yeast two-hybrid procedure, the gene of interest or parts thereof (BAIT), is cloned in such a way that it is expressed as a fusion to a peptide that has a DNA binding domain. A second gene, or number of genes, such as those from a cDNA library (TARGET), is cloned so that it is expressed as a fusion to an activation domain. Interaction of the protein of interest with its binding partner brings the DNA-binding peptide together with the activation domain and initiates transcription of the reporter genes. The first reporter gene will select for yeast cells that contain interacting proteins (this reporter is usually a nutritional gene required for growth on selective media). The second reporter is used for confirmation and while being expressed in response to interacting proteins it is usually not required for growth.

The nature of the $GABA_A$ receptor interacting genes and proteins can also be studied such that these partners can also be targets for drug discovery.

Structural Studies $GABA_A$ receptor recombinant proteins can be produced in bacterial, yeast, insect and/or mammalian cells and used in crystallographical and NMR studies. Together with molecular modelling of the protein, structure-driven drug design can be facilitated.

EXAMPLE 8

Generation of Polyclonal Antibodies Against the $GABA_A$ Receptor or $GABA_A$ Receptor Subunits Following the identification of mutations in the GABRG2 subunit of the $GABA_A$ receptor in individuals with childhood absence epilepsy, febrile seizures (including FS$^+$) and myoclonic epilepsy and therefore confirming the involvement of the receptor in epilepsy, antibodies can be made to selectively bind and distinguish mutant from normal protein. Antibodies specific for mutagenised epitopes are especially useful in cell culture assays to screen for cells which have been treated with pharmaceutical agents to evaluate the therapeutic potential of the agent.

To prepare polyclonal antibodies, short peptides can be designed homologous to a particular $GABA_A$ receptor subunit amino acid sequence. Such peptides are typically 10 to 15 amino acids in length. These peptides should be designed in regions of least homology to other receptor subunits and should also have poor homology to the mouse orthologue to avoid cross species interactions in further down-stream experiments such as monoclonal antibody production. Synthetic peptides can then be conjugated to biotin (Sulfo-NHS-LC Biotin) using standard protocols supplied with commercially available kits such as the PIERCE™ kit (PIERCE). Biotinylated peptides are subsequently complexed with avidin in solution and for each peptide complex, 2 rabbits are immunized with 4 doses of antigen (200 μg per dose) in intervals of three weeks between doses. The initial dose is mixed with Freund's Complete adjuvant while subsequent doses are combined with Freund's Immuno-adjuvant. After completion of the immunization, rabbits are test bled and reactivity of sera is assayed by dot blot with serial dilutions of the original peptides. If rabbits show significant reactivity compared with pre-immune sera, they are then sacrificed and the blood collected such that immune sera can be separated for further experiments.

This procedure is repeated to generate antibodies against wild-type forms of receptor subunits. These antibodies, in conjunction with antibodies to mutant $GABA_A$ receptor subunits, are used to detect the presence and the relative level of the mutant forms in various tissues.

EXAMPLE 9

Generation of Monoclonal Antibodies Specific for the $GABA_A$ Receptor or $GABA_A$ Receptor Subunits Monoclonal antibodies can be prepared in the following manner. Immunogen comprising an intact $GABA_A$ receptor subunit protein or $GABA_A$ receptor subunit peptides (wild type or mutant) is injected in Freund's adjuvant into mice with each mouse receiving four injections of 10 to 100 ug of immunogen. After the fourth injection blood samples taken from the mice are examined for the presence of antibody to the immunogen. Immune mice are sacrificed, their spleens removed and single cell suspensions are prepared (Harlow and Lane, 1988). The spleen cells serve as a source of lymphocytes, which are then fused with a permanently growing myeloma partner cell (Kohler and Milstein, 1975). Cells are plated at a density of $2\times10^5$ cells/well in 96 well plates and individual wells are examined for growth. These wells are then tested for the presence of GABA receptor subunit specific antibodies by ELISA or RIA using wild type or mutant subunit target protein. Cells in positive wells are expanded and subcloned to establish and confirm monoclonality. Clones with the desired specificity are expanded and grown as ascites in mice followed by purification using affinity chromatography using Protein A Sepharose, ion-exchange chromatography or variations and combinations of these techniques.

INDUSTRIAL APPLICABILITY

The present invention allows for the diagnosis and treatment of epilepsy and/or anxiety and/or manic depression and/or phobic obsessive symptoms and/or Alzheimer's disease and/or schizophrenia and/or migraine and/or obesity. In particular, the present invention allows for the diagnosis and treatment of generalised epilepsy and more particularly childhood absence epilepsy, febrile seizures (including $FS^+$) and/or myoclonic epilepsy.

TABLE 1

Splice Sites of the GABRG2 Gene

| Exon | Size (bp) | 3' Splice site (intron/exon) | Consensus strength (%) | 5' Splice site (exon/intron) | Consensus strength (%) | Intron size (bp) |
|------|-----------|------------------------------|------------------------|------------------------------|------------------------|------------------|
| 1 | 333 | 5'UTR | | TCTACCCTGG/gtaagatgtg (SEQ ID NO:52) | 86.49 | 25.717 |
| 2 | 152 | tttttcttag/CTTCACTAGC (SEQ ID NO:53) | 83.08 | GATATAGGAG/gtttgttaaa (SEQ ID NO:54) | 78.65 | 1.515 |
| 3 | 68 | ctctttacag/TGAAGCCAAC (SEQ ID NO:55) | 92.66 | TATCAATATG/gtgagtttcc (SEQ ID NO:56) | 88.87 | 20.75 |
| 4 | 221 | attaaaacag/GAATACACTA (SEQ ID NO:57) | 87.50 | ACTCCCTAAG/gtcatagaac (SEQ ID NO:58) | 69.89 | 3.376 |
| 5 | 83 | ttctacttag/GTTGACAATT (SEQ ID NO:59) | 86.35 | TTCTCCAGTT/gtaagtaata (SEQ ID NO:60) | 79.38 | 2.571 |
| 6 | 138 | ctcacggcag/ATGGCTATCC (SEQ ID NO:61) | 84.13 | ACAACTTCCG/gtaagatgca (SEQ ID NO:62) | 86.13 | 38.145 |
| 7 | 153 | tctgttccag/GAGATTATGT (SEQ ID NO:63) | 90.93 | ACATCTTTAG/gtgagacacc (SEQ ID NO:64) | 91.05 | 6.791 |
| 8 | 206 | ctctcttcag/GTATCACCAC (SEQ ID NO:65) | 90.62 | GAAAAACCCT/gtatgtatca (SEQ ID NO:66) | 67.70 | 3.779 |
| 9 | 391 | ctcgtcccag/GCCCCTACCA (SEQ ID NO:67) | 91.25 | 3'UTR | | |

TABLE 2

Primers Used for SSCP Analysis of GABRG2 in Family 1

| Exon | Forward (5' - 3') | Reverse (5' - 3') |
|------|-------------------|-------------------|
| 1 | GCATGAGTATACACGAGTGTGC (SEQ ID NO:7) | GTAAAGCCGCACATCCTAGGAG (SEQ ID NO:8) |
| 2 | CAGTTAGTCTCCATCTATGCAG (SEQ ID NO:9) | CCTTGCTCTTGAACTACACTG (SEQ ID NO:10) |
| 3 | TATGCGTGCTTGGTGCATGTGC (SEQ ID NO:11) | GGATCTGGAAGACTATCTTTCAC (SEQ ID NO:12) |

TABLE 2-continued

Primers Used for SSCP Analysis of GABRG2 in Family 1

| Exon | Forward (5' - 3') | Reverse (5' - 3') |
|---|---|---|
| 4 | GTGAGACAGTAACCTCCTCAGC (SEQ ID NO:13) | GATAGCATGCCAACCCTGATGC (SEQ ID NO:14) |
| 5 | CCTGGACTTGGTGGATTTCTTC (SEQ ID NO:15) | TCACCCTAATCGGAGCAAGCTG (SEQ ID NO:16) |
| 6 | TGCCCTTTGGTCCAAGATCCTC (SEQ ID NO:17) | CTGTGTGAAATGTGGCGATTTC (SEQ ID NO:18) |
| 7 | GGGATTCAGTTCAGGTTGTG (SEQ ID NO:19) | GGGTTGGTTCCAAGTCTTTGC (SEQ ID NO:20) |
| 8 | CCACTTATACCTCCTTTCCC (SEQ ID NO:21) | CGTTATGGCCTGGCTAAACTC (SEQ ID NO:22) |
| 9 | CATCACATTGGTGACATTGTGG (SEQ ID NO:23) | CCACTACTGTAAATAGTCAGGGC (SEQ ID NO:24) |

TABLE 3

Primers Used for SSCP Analysis of GABRG2 in Family 2

| Exon | Forward (5' - 3') | Reverse (5' - 3') |
|---|---|---|
| 1A | GCATGAGTATACACGAGTGTGC (SEQ ID NO:7) | GCCTCTTGGTTGCAGAAGAATC (SEQ ID NO:25) |
| 1B | CAGTGAAGGACCTACTAGAGG (SEQ ID NO:26) | GTAAAGCCGCACATCCTAGGAG (SEQ ID NO:8) |
| 2 | CAGTTAGTCTCCATCTATGCAG (SEQ ID NO:9) | CCTTGCTCTTGAACTACACTG (SEQ ID NO:10) |
| 3 | TATGCGTGCTTGGTGCATGTGC (SEQ ID NO:11) | GGATCTGGAAGACTATCTTTCAC (SEQ ID NO:12) |
| 4 | GTGAGACAGTAACCTCCTCAGC (SEQ ID NO:13) | GATAGCATGCCAACCCTGATGC (SEQ ID NO:14) |
| 5 | CCTGGACTTGGTGGATTTCTTC (SEQ ID NO:15) | TCACCCTAATCGGAGCAAGCTG (SEQ ID NO:16) |
| 6 | TGCCCTTTGGTCCAAGATCCTC (SEQ ID NO:17) | TCAACTCTGGAAGGGTCACTTG (SEQ ID NO:27) |
| 7 | GGGATTCAGTTCAGGTTGTG (SEQ ID NO:19) | GGGTTGGTTCCAAGTCTTTGC (SEQ ID NO:20) |
| 8 | CCACTTATACCTCCTTTCCC (SEQ ID NO:21) | CGTTATGGCCTGGCTAAACTC (SEQ ID NO:22) |
| 9A | CATCACATTGGTGACATTGTGG (SEQ ID NO:23) | ACATCTCTCCATGAGACTCAGT (SEQ ID NO:28) |
| 9B | TATTGGGTCTCCTACCTCTACC (SEQ ID NO:29) | CCACTACTGTAAATAGTCAGGGC (SEQ ID NO:24) |

Note; All primers were labeled at their 5' ends with HEX for the SSCP analysis or Family 2. Exons 1 and 9 were split into 2 overlapping amplicons due to the large size of these exons.

TABLE 4

Primers Used for SSCP Analysis of GABRD in Family 3

| Exon | Forward (5' - 3') | Reverse (5' - 3') |
|---|---|---|
| 2 | CAGAACAGTGCTGCATCCC (SEQ ID NO:30) | CCTAGAGGCCAGCCTACA (SEQ ID NO:31) |
| 3 | TCCCATCGTGGCTCCCATGCT (SEQ ID NO:32) | TCATGGTGTACTCCTGTGGAG (SEQ ID NO:33) |
| 4A | CACATCTCAGAGGCCAACATG (SEQ ID NO:34) | AGCCACAGCTTGTCCACGAAG (SEQ ID NO:35) |
| 4B | CTACAACCACACCAACGAGAC (SEQ ID NO:36) | TTCCAAGCCTTGGAGCGTCCA (SEQ ID NO:37) |
| 5 | AACACAGTCTGAGAAGTAGC (SEQ ID NO:38) | GCTTTCCTGCATCCTGAGC (SEQ ID NO:39) |
| 6 | CCACCTGTGTGCTTTTCCTC (SEQ ID NO:40) | AAGCATGAAAACCACAGGCG (SEQ ID NO:41) |
| 7 | TGAGTCCCATGGTTGGGCTG (SEQ ID NO:42) | AGGGATGGGGAGTCCTGTTC (SEQ ID NO:43) |
| 8 | TACGACAATGGCACCACCTG (SEQ ID NO:44) | CAGTGCTGTCCCTGGCTC (SEQ ID NO:45) |
| 9A | ATGGGAACACCTGTGGTCCA (SEQ ID NO:46) | CTTCTTCGTCTCCCCTGTCT (SEQ ID NO:47) |
| 9B | TGATGGGCTCCTACAGGTCG (SEQ ID NO:48) | TTCTCCCAGGAAGTTTCTGG (SEQ ID NO:49) |

Note: All primers were labelled at their 5' ends with HEX for the SSCP analysis oF Family 3. Exons 4 and 9 were split into 2 overlapping amplicons due to the large size of these exons. Exon 1 was not screened due to the lack of genomic sequence in available databases flanking this exon.

REFERENCES

References cited herein are listed on the following pages, and are incorporated herein by this reference.

Annegers, J F. (1996). *The treatment of epilepsy: Principles and practice*. Second Edition. (Wyllie E (Ed) Williams and Wilkins).
Berkovic, S F. et al. (1987). *Neurology* 37: 993–1000.
Berkovic, S F. Et al. (1994). *The epilepsies: specific syndromes or a neurobiological continuum?* In: Epileptic seizures and syndromes (Wolf (Ed) London: John Liddey). 25–37.
Biervert, C. et al. (1998). *Science* 279: 403–406.
Blasi, C. (2000). *Prog. Neuropsychopharmacol.* 24: 561–577.
Brooks-Kayal, A R. And Pritchett, D B. (1993). *Ann. Neurol.* 34: 687–693.
Charlier, C. et al. (1998). *Nat. Genet.* 18: 53–55.
Cole, S P. et al. (1984). *Mol. Cell Biol.* 62: 109–120.
Commission on Classification and Terminology of the International League Against Epilepsy. (1989). *Epilepsia.* 30: 389–399.
Cote, R J. et al. (1983). *Proc. Natl. Acad. Sci. USA* 80: 2026–2030.
Culver, K. (1996). *Gene Therapy: A Primer for Physicians*. Second Edition. (Mary Ann Liebert).
Destexhe, A. (1999). *Eur. J. Neurosci.* 11: 2175–2181.
Draguhn, A. et al. (1990). *Neuron* 5: 781–788.
Feucht, M. et al. (1999). *Biol. Psychiatry* 46: 997–1002.

Friedman, T. (1991). In *Therapy for Genetic Diseases*. (T Friedman (Ed) Oxford University Press. pp 105–121.
Futatsugi, Y. and Riviello, J J. (1998). *Brain Develop.* 20: 75–79.
Gardiner, M. (2000). *J Neurol.* 247: 327–334.
Gerner, R H. And Hare, T A. (1981). *Am. J. Psychiatry* 138: 1098–1101.
Goldman, C K. et al. (1997). *Nature Biotechnology* 15: 462–466.
Harlow, E. and Lane, D. (1988). *Antibodies: A Laboratory Manual* (Cold Spring Harbor Laboratory, Cold Spring Harbor, N.Y.).
Heller, R A. et al. (1997). *Proc. Natl. Acad. Sci. USA* 94: 2150–2155.
Huse, W D. et al. (1989). *Science* 246: 1275–1281.
Jackson, M B. (1999). *Jasper's Basic Mechanisms of the Epilepsies, Third Edition: Advances in Neurology* 79: 511–524.
Kohler, G. and Milstein, C. (1975). *Nature* 256: 495–497.
Kozbor, D. et al. (1985). *J. Immunol. Methods* 81:31–42.
Kucken, A M. et al. (2000). *Mol. Pharmacol.* 57: 932–939.
Lathrop, G M. and Lalouel, J M. (1984). *Am. J. Hum. Genet.* 36: 460–465.
Limroth, V. et al. (1996). *Br. J. Pharmacol.* 117: 99–104.
Mitsikostas, D D. and Sanchez del Rio, M. (2001). *Brain Res. Brain Res. Rev.* 35: 20–35.
Mizukami, K. et al. (1998a). *Brain Res. Mol. Brain Res.* 56: 268–272.
Mizukami, K. et al. (1998b). *Brain Res.* 799: 148–155.
Olsen, R W. et al. (1999). *Jasper's Basic Mechanisms of the Epilepsies, Third Edition: Advances in Neurology* 79: 511–524.
Orlandi, R. et al. (1989). *Proc. Natl. Acad. Sci. USA* 86: 3833–3837.
Papadimitriou, G N. et al. (1998). *Am. J. Med. Genet.* 81: 73–80.
Pearlson, G D. (2000). *Ann. Neurol.* 48: 556–566.
Phillips, H A. et al. (1995). *Nature Genet.* 10: 117–118.
Reutens, D C. ahnd Berkovic, S P. (1995). *Neurology* 45: 1469–1476.
Roger, J. et al. (1992). *Epileptic syndromes in infancy, childhood and adolescence*. Second Edition. (John Libbey, London).
Scharf, D. et al. (1994). *Results Probl. Cell Differ.* 20: 125–162.
Scheffer, I E. and Berkovic, S F. (1997). *Brain* 120: 479–490.
Schena, M. et al. (1996). *Proc. Natl. Acad. Sci. USA* 93: 10614–10619.
Sibille, E. et al. (2000). *J. Neurosci.* 20: 2758–2765.
Sigel, E. and Buhr, A. (1997). *Trends Pharmacol. Sci.* 18: 425–429.
Singh, N A. et al. (1998). *Nat. Genet.* 18: 25–29.
Sutton, G C. (1990). *The principles and practice of medical genetics*. Second Edition. (Churchill Livingstone, N.Y.).
Vergnes, M. et al. (2000). *Exp. Neurol.* 161: 714–723.
Wallace, R. et al. (1998). *Nature Genet.* 19: 366–370.
Wallace, R. et al. (2001). *Nature Genet.* 28: 49–52.
Winter, G. et al. (1991). *Nature* 349: 293–299.
Wyman, A R and White, R. (1980). *Proc. Natl. Acad. Sci.* 77: 6754–6758.

The invention claimed is:

1. An isolated human DNA molecule encoding a mutant γ-aminobutyric acid type A (GABA$_A$) gamma-2 subunit, wherein a mutation event has created a phenotype of epilepsy and/or febrile seizures, wherein said mutation event results in replacement of a highly conserved arginine at residue 43 of the mature gamma-2 subunit with another amino acid residue.

2. An isolated human DNA molecule as claimed in claim 1 wherein said mutation event results in replacement of the highly conserved arginine with a glutamine.

3. An isolated human DNA molecule as claimed in claim 2 wherein said mutation event is a G→A nucleotide substitution at a position of the DNA sequence encoding the gamma-2 subunit corresponding to position 471 of SEQ ID NO:1.

4. An isolated human DNA molecule as claimed in claim 3 having the nucleotide sequence set forth in SEQ ID NO:1.

5. An isolated mammalian DNA molecule comprising the nucleotide sequence set forth in SEQ ID NO:1.

6. An isolated mammalian DNA molecule consisting of the nucleotide sequence set forth in SEQ ID NO:1.

7. An isolated human DNA molecule encoding a mutant γ-aminobutyric acid type A (GABA$_A$) gamma-2 subunit, wherein a mutation event has created a phenotype of epilepsy and/or febrile seizures, wherein said mutation event is a C→T nucleotide substitution at a position of the DNA sequence encoding the gamma-2 subunit corresponding to position 1394 of SEQ ID NO:2.

8. An isolated human DNA molecule as claimed in claim 7 wherein said mutation event results in the introduction of a stop codon at a position of the DNA sequence encoding the encoded mature gamma-2 subunit protein corresponding to position 351 of SEQ ID NO:5.

9. An isolated human DNA molecule as claimed in claim 8 which has the nucleotide sequence set forth in SEQ ID NO:2.

10. An isolated mammalian DNA molecule comprising the nucleotide sequence set forth in SEQ ID NO:2.

11. An isolated mammalian DNA molecule consisting of the nucleotide sequence set forth in SEQ ID NO:2.

12. An isolated human DNA molecule encoding a mutant γ-aminobutyric acid type A (GABA$_A$) delta subunit, wherein a mutation event has created a phenotype of epilepsy and/or febrile seizures, wherein the mutation event results in replacement of an arginine residue at position 172 of the encoded mature protein with another amino acid residue.

13. An isolated human DNA molecule as claimed in claim 12 wherein the arginine residue is replaced with a cysteine residue.

14. An isolated human DNA molecule as claimed in claim 13 wherein said mutation event is a C→T nucleotide substitution at a position of the DNA sequence encoding the delta subunit corresponding to position 658 of SEQ ID NO:3.

15. An isolated human DNA molecule as claimed in claim 14 in which the nucleotide sequence is as set forth in SEQ ID NO:3.

16. An isolated mammalian DNA molecule comprising the nucleotide sequence set forth in SEQ ID NO:3.

17. An isolated mammalian DNA molecule consisting of the nucleotide sequence set forth in SEQ ID NO:3.

* * * * *